United States Patent [19]

Liu et al.

[11] Patent Number: 5,721,217
[45] Date of Patent: Feb. 24, 1998

[54] DEOXY AND OXYGEN-SUBSTITUTED SUGAR-CONTAINING 14-AMINOSTEROID COMPOUNDS

[75] Inventors: Song Liu; David Edward Portlock, both of Norwich, N.Y.; Gilles Yves Genain, Wyoming, Ohio; Jean-Jacques Koenig, Maisons Lafitte; Jacques de Rostolan, Gif Sur Yvette, both of France

[73] Assignee: The Procter & Gamble Company, Cincinnati, Ohio

[21] Appl. No.: 460,348

[22] Filed: Jun. 2, 1995

Related U.S. Application Data

[63] Continuation of Ser. No. 299,456, Sep. 6, 1994, abandoned, which is a continuation-in-part of Ser. No. 126,476, Sep. 24, 1993, abandoned.

[51] Int. Cl.$^6$ .................... A61K 31/705; C07H 15/24
[52] U.S. Cl. .................... 514/26; 514/182; 514/821; 514/824; 536/5; 536/18.5
[58] Field of Search .................... 514/26, 182, 821, 514/824; 536/5, 18.5

[56] References Cited

U.S. PATENT DOCUMENTS

| | | | |
|---|---|---|---|
| 4,552,868 | 11/1985 | Jarreau et al. | 514/26 |
| 4,584,289 | 4/1986 | Jarreau et al. | 514/182 |
| 4,885,280 | 12/1989 | Jarreau et al. | 514/26 |

FOREIGN PATENT DOCUMENTS 9305790  4/1993  WIPO.

*Primary Examiner*—John Kight
*Assistant Examiner*—Howard C. Lee
*Attorney, Agent, or Firm*—Mary P. McMahon; Karen F. Clark; Jacobus C. Rasser

[57] ABSTRACT

Disclosed are 14-aminosteroid compounds, including pharmaceutically acceptable acid salts and esters thereof, useful in treating individuals afflicted with congestive heart failure, which compounds have the general formula:

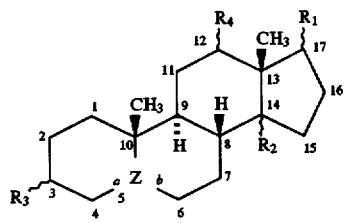

wherein $R_3$ is a deoxy or oxygen-substituted monosaccharide sugar residue and $R_1$, $R_2$ and $R_4$ are various other substituents as defined herein.

37 Claims, No Drawings

DEOXY AND OXYGEN-SUBSTITUTED SUGAR-CONTAINING 14-AMINOSTEROID COMPOUNDS

This is a continuation of application Ser. No. 08/299,456, filed Sep. 6, 1994, now abandoned which is a continuation-in-part of application Ser. No. 08/126,476 filed Sep. 24, 1993, now abandoned.

BACKGROUND OF THE INVENTION

This invention relates to novel deoxy and oxygen-substituted sugar-containing 14-aminosteroid compounds. This invention also relates to pharmaceutical compositions containing these novel compounds as well as to a method of treating Congestive Heart Failure (CHF) using the compounds of the present invention.

CHF is a progressive disease wherein the heart is increasingly unable to supply adequate cardiac output (CO), which is the volume of blood pumped by the heart over time, to deliver the oxygenated blood to the peripheral tissues. When the heart initially fails, the rest of the body compensates for the loss in CO and such compensatory mechanisms eventually result in the syndrome known as CHF. As CHF progresses, structural and hemodynamic damages occur. Such structural damage manifests itself macroscopically as ventricular hypertrophy in the myocardium, and microscopically as interstitial, perivascular and replacement fibrosis in the ventricle wall, decreased myocardial capillary density, and myocardial cell death. When fibrosis of the myocardial tissue occurs it compromises the functioning of the heart because the remaining viable myocardial cells have a greater workload.

Hemodynamically, in the failing heart, the capacity to develop force during systole (the phase in the cardiac cycle during which ejection of blood from the ventricles occurs) is reduced. Thus, a greater end-diastolic volume (during the diastolic phase of the cardiac cycle filling of the ventricles occurs) is needed to perform any given level of external work. In cardiac failure, reduced ejection, caused by a mismatch of work capacity and load, results in an increase in end diastolic pressure and pulmonary capillary pressure. Pulmonary congestion and peripheral edema often follow. From the patient's perspective, as CHF progresses, the patient experiences increasingly worsening symptoms of fatigue and dyspnea.

Effective treatment of CHF requires a determination of its etiology, if possible, because some CHF etiologies have their own unique form of treatment. CHF has a variety of etiologies, including diseases of the myocardium such as coronary artery disease or myocarditis; diseases of the valves, such as mitral valve prolapse or aortic stenosis; pericardial diseases; congenital heart disease; pulmonary disease, cardiac arrhythmias, hypertension, and diabetes. For example, if the etiology of CHF is myocarditis or an arrhythmia, then treating the patient with an antimicrobial or an antiarrhythmic agent, respectively, may restore the patient to normal cardiac function.

However, once the etiologies not responding to other treatments have been ruled out, treatment by one or more of three modalities is initiated: 1) improvement of the heart's pumping capacity by administration of an inotropic agent, such as digitalis, 2) reduction of the heart's workload by rest and/or by administration of vasodilators such as captopril, and 3) controlling sodium and water retention by a low sodium diet or administration of a diuretic such as thiazide. Treatment of CHF is individualized according to the patients symptomatology and tolerance for certain medications. For example, some patients may have a strong tendency to develop digitalis toxicity, while other patients with mild symptoms may benefit from diuretics which have a greater therapeutic index. Moreover, current wisdom suggests that diuretics are appropriate first line CHF therapy and that diuretic treatment should be followed by vasodilators and digitalis. It has also been noted that digitalis is most effective in patients suffering from severe CHF. See generally, Braunwald, *Heart Disease: A Textbook of Cardiovascular Medicine*, Vol. (3rd ed. 1988), Chung, E. K., *Quick Reference to Cardiovascular Disease*, Chapter 27 (2d ed. 1983) and Fowler, N. O., *Cardiac Diagnosis and Treatment*, Chapter 12 (2d ed. 1976).

While digitalis is useful for ameliorating the symptoms associated with the hemodynamic problems characteristic of severe CHF, its low therapeutic index, in effect, limits its therapeutic utility. See generally, Braunwald, *Heart Disease: A Textbook of Cardiovascular Medicine*, Vol. (3rd ed. 1988), Chung, E. K., *Quick Reference to Cardiovascular Disease*, Chapter 27 (2d ed. 1983) and Fowler, N. O., *Cardiac Diagnosis and Treatment*, Chapter 12 (2d ed. 1976) and Goodman and Gilman, *The Pharmacological Basis of Therapeutics*, Chapter 34 (8th ed., 1990).

The toxicity problems associated with digitalis have prompted investigators to attempt to develop safer cardioactive compounds. Cardioactive steroid nucleus containing compounds have been described in the following patents: World Patent Publication WO 87/04167 to Chiodini, et al. published Jul. 16, 1987 describes aminoglycoside steroid derivatives substituted by an amino-sugar residue at the 3-position and an acetal linkage at the 14-position. The disclosure states that the compounds are useful for the treatment of hypertension. French Patent 2,642,973 of Guina published Aug. 17, 1990 describes a digitalis-like compound, 2,3-dioxymethyl-6-methyl-3-beta-D-glucose-strophanthidine, which contains the steroid nucleus substituted at the 3-position with a glucose moiety and at the 17-position with the lactone moiety, and at the 14-position with a hydroxyl group. The disclosure states that the compound is useful in preventing pathologic states resulting from cardiac insufficiencies for which digitalis is prescribed and for preventing pathologic states resulting from hypertension due to arterial calcification. The Guina compound is also alleged to be a positive inotrope, a peripheral vasodilator, and an antiarrhythmic agent. World Patent Publication WO 87/04168 to Chiodini et al., Jul. 16, 1987 discloses an aminoglycoside steroid having an alkyl substituted amino sugar at the 3-position, such as 2-amino or 2-alkylamino-2-deoxy-hexopyranosyl, 3-amino or 3-alkylamino-3-deoxy-hexo-pyranosyl, 3-amino or 3-alkyl-amino-3,6-dideoxy-hexopyranosyl, 3 amino or 3-alkylamino-2,3,6-trideoxy-hexopyranosy 4-amino or 4-alkylamino 2,4,6-trideoxy-hexopyranosyl residues, and a cyclic amide (lactam) at the 17-position. The 14-position is substituted with a hydrogen. The compound is said to be useful as an antihypertensive. Word Patent Publication WO 91/17176 to Kenny, et al. published Nov. 14, 1991, discloses a steroid glycoside, useful as a pressor agent, having a sugar moiety at the 3-position, such as a pentose, hexose or combinations thereof, and a lactone ring at the 17-position, the 14-position is substituted with an OH, H or a F, Cl, Br or $NH_2$; and DD 296502 A5 to Siemann, et al. granted Dec. 5, 1991 discloses a steroid amide for treating cardial insufficiency wherein the 3-position is substituted with a sulphonyl amino group and the 17-position is substituted with a 5 or 6-membered lactone ring; the 14-position is substituted with a hydroxy group. U.S. Pat. No. 5,144,017 to LaBella, Sep. 1, 1992 discloses steroid compounds said to be useful as cardiac stimulants wherein the 3-position is substituted with a glycoside radical such as β-D-glucoside, α-L-rhamnoside, tridigitoxoside and the 17-position is substituted with an acetoxy group or an amino group; and the 14-position has a hydroxy group; and U.S. Pat. No. 5,175,281 to McCall, Dec. 29, 1992 discloses pyrimidinylpiperazinyl steroid compounds useful in treating spinal trauma, head injury and the subsequent cerebral vasospasm, preventing damage following cardiopulmonary resuscitation and cardiac infarction wherein the 3-position is hydroxy, $CH_3O$, COOH, or benzoxy, the 14-position is a hydrogen and the 17-position is a heterocyclic amine. DD 256,134 A1 to Wunderwald, et al., granted Apr. 27, 1988 discloses a process for making cardioactive steroids wherein the 3-position of the steroid molecule is substituted with a morpholinoformyloxy residue, and the 17-position of the steroid molecule is substituted with a lactone ring; and the 14-position is substituted with hydroxy, hydrogen or an olefin. Said compounds are alleged to be useful for increasing cardiac contractility. JP 4-290899 to Ichikawa, et al., laid open Oct. 15, 1992, discloses a cardiotonic steroid compound wherein the 3-position of the steroid nucleus is substituted with an oligosaccharide; wherein further said oligosaccharide consists of three glucopyranosyl moieties and the 14-position is substituted with an OH group, and the 17-position is substituted with a lactone ring. Templeton, et al., 36 *J. Med. Chem.* 42–45 (1993) disclose the synthesis of derivatives of 14-hydroxy-21-nor-5β, 14β-pregnane and 5β, 14β-pregnane C-3 α-L-rhamnosides and tris-β-D-digitoxosides. Said compounds are reported to be effective cardiotonics. These derivatives, possessing a C-17β $COCH_2OH$, $CH_2OH$, $CO_2H$, $CO_2Me$, $CH_2NH_2$, or $CH_2NO_2$ group, bind to the digitalis receptor recognition site of heart muscle. Templeton, et al., 1 *J. Chem. Sci. Perkin. Trans.*, 2503–2517 (1992) disclose the synthesis of 20α- and 20β-acetamido-, amino-, nitro- and hydroxy-3β-glycoside (α-L-rhamnopyranoside and tris-β-D-digitoxoside) and genin derivatives of 14-hydroxy-5β, 14β-pregnane together with the C-20 oxime, hydrazone and amidinohydrazone. These compounds are asserted to be effective cardiotonics. Adeoti, S. B., et al., 12 *Tetrahedron Letters*, 3717–3730 (1989) disclose a method for introducing a 14β-amino function into a steroid molecule. Said method allows for the preparation of the cardioactive 14β-amino-5β-pregnane-3β, 20b diol.

Additionally, angiotensin converting enzyme inhibitors (ACEI) have been shown to reduce mortality in CHF patients. See, Nicklas, J. M. and Pitt, B., et al. (The SOLVD Investigators), "Effect of Enalapril on Survival in Patients with Reduced Left Ventricular Ejection Fractions and Congestive Heart Failure", *N. Engl. J. Med.* 325(5):293 (1991).

Nevertheless, four million people still suffer from CHF. The five year mortality after diagnosis of CHF is 60% for men and 45% for women. This is a clear indication that better therapies directed toward treating CHF are needed. See, Parmley, W. W., "Pathophysiology and Current Therapy of Congestive Heart Failure", *J. Am. Col. Cardiol.* 13:771–785 (1989); Francis, G. S. et al., "Congestive Heart Failure: Pathophysiology and Therapy," *Cardiovascular Pharmacology*, 3rd Edition (1990).

The 14-aminosteroid compounds have been shown to be useful in treating CHF by increasing cardiac contractility. These compounds provide the therapeutic benefit of increased cardiac contractility without the side effects of digitalis. These 14-aminosteroids are described in the following three patents, all incorporated by reference herein:

U.S. Pat. No. 4,552,868, Jarreau, et al., issued Nov. 12, 1985; U.S. Pat. No. 4,584,289, Jarreau, et al., issued Apr. 22, 1986 and U.S. Pat. No. 4,885,280, Jarreau, et al., issued Dec. 5, 1989. These three patents describe 14-aminosteroid compounds possessing positive inotropic activity. It has now been discovered that the 14-aminosteroid compounds of the present invention, wherein the 3-position is substituted with a deoxy and an oxygen-substituted sugar moiety, are more effective inotropes. Said deoxy and oxygen-substituted sugar-containing 14-aminosteroids are more resistant to metabolism and therefore provide a longer duration of inotropic activity than the prior art 14-aminosteroids.

SUMMARY OF THE INVENTION

Deoxy and oxygen-substituted sugar containing 14-aminosteroid compounds and the pharmaceutically-acceptable acid salts or esters thereof of the general formula:

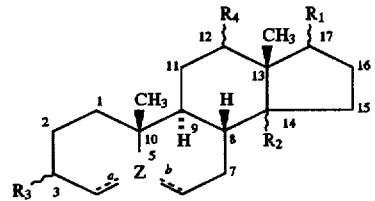

wherein
a) $R_1$ is
(i) $COOR_5$, where
  $R_5$ is a 1–6 carbon lower alkyl group; a 1–6 carbon lower alkyl group substituted by an amino group; an arylalkyl or heteroarylalkyl group or a carbocyclic ring, or
(ii) $CHR_6OH$, where
  $R_6$ is a hydrogen atom or a 1–6 carbon lower alkyl group, or
(iii) $COR'''$, where
  $R'''$ is hydrogen; 1–6 carbon lower alkyl; 1–6 carbon lower alkyl substituted amino; amino or dialkylamino, and
b) $R_2$ is $-NR_7R_8$; where $R_7$ and $R_8$; which may be the same or different, are hydrogen atoms or 1–6 carbon lower alkyl group, and
c) $R_3$ is
(i) a deoxy or oxygen-substituted monosaccharide sugar residue,

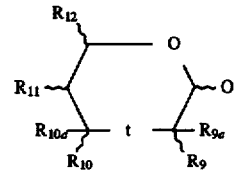

wherein $R_{9a}$, $R_9$, $R_{10}$, and $R_{10a}$, which may be the same or different; are 1–6 carbon lower alkyl; hydrogen; hydroxy; fluorine; alkoxy; acetoxy; arylalkyloxy; or benzoxy; $R_{11}$ is 1–6 carbon lower alkyl; hydrogen; hydroxy; fluorine; benzoxy; arylalkyloxy; heteroarylalkyloxy; acetoxy or alkoxy; wherein further when $R_5$ is 1–6 carbon lower alkyl; either $R_9$, $R_{10}$, or $R_{11}$ cannot be hydroxy or acetoxy; further provided that when $R_{9a}$ is hydrogen and $R_{10a}$ is hydrogen and $R_9$ is hydrogen; hydroxy or acetoxy; and $R_{11}$ is hydroxy; acetoxy or alkoxy; $R_{10}$ cannot be hydroxy or acetoxy; and $R_{12}$ is methyl; acetoxymethyl or hydroxymethyl; t can be a single or double bond, or (ii) a deoxy or oxygen-substituted monosaccharide sugar residue,

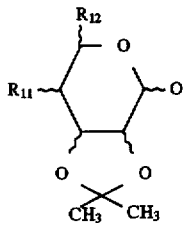

wherein $R_{11}$ is arylalkyloxy; heteroarylalkyloxy or 1–6 carbon lower alkyl substituted oxosilane and $R_{12}$ is methyl, and d) $R_4$ is
   (i) OH, or
   (ii) H, or
   (iii) $OR_{13}$, where $R_{13}$ is a monosaccharide sugar residue; acetoxy; benzoxy; arylalkyl or heteroarylalkyl, and e) Z is
   (i) —CH—, where a and b are single bonds, or
   (ii) =C, where either a or b is a double bond.

DEFINITIONS AND USAGE OF TERMS

The following is a list of definitions for terms used herein.

"Aminosteroid" is a steroid ring compound having an amino group on the steroid nucleus.

"Alkyl" is an unsubstituted or substituted, straight-chain, cyclic or branched, saturated hydrocarbon chain having 1 to 8 carbon atoms, and preferably, unless otherwise stated, from 1 to 4 carbon atoms. Preferred alkyl groups include, but are not limited to methyl, ethyl, propyl, isopropyl, and butyl; a monovalent radical derived from an aliphatic hydrocarbon by removal of 1H; as methyl. A lower alkyl group contains 1–6 carbon atoms.

"Heteroalkyl" as used herein is an unsubstituted or substituted, saturated chain having from 3 to 8-members and comprising carbon atoms and one or two heteroatoms.

"Alkenyl" is an unsubstituted or substituted, straight-chain or branched, hydrocarbon chain having from 2 to 8 carbon atoms, preferably from 2 to 4 carbon atoms, and having at least one olefinic double bond.

"Alkynyl" is an unsubstituted or substituted, straight-chain or branched, hydrocarbon chain having from 2 to 8 carbon atoms, preferably from 2 to 4 carbon atoms, and having at least one triple bond.

"Acetate": A salt of acetic acid containing the $CH_3COO$— radical.

"Acetoxy": Acetyloxy. The radical $CH_3COO$—.

"Acetyl": The acyl radical $CH_3CO$—.

"Aglycone": That component of a glycoside, e.g., plant pigment, which is not a sugar.

"Carbocyclic ring" or "Carbocycle" as used herein is an unsubstituted or substituted, saturated, unsaturated or aromatic, hydrocarbon ring, generally containing from 3 to 8 atoms, preferably 5 to 7 atoms.

"Heterocyclic ring" or "Heterocycle" as used herein is an unsubstituted or substituted, saturated or unsaturated or aromatic ring comprised of carbon atoms and one or more heteroatoms in the ring. Heterocyclic rings generally contain from 3 to 8, preferably 5 to 7, atoms. Unless otherwise stated, the heteroatom may be independently chosen from nitrogen, sulfur, and oxygen.

"Aryl" is an aromatic carbocyclic ring. Aryl groups include, but are not limited to, phenyl, tolyl, xylyl, cumenyl, and naphthyl; an organic radical derived from an aromatic hydrocarbon by the removal of one atom; e.g. phenyl from benzene.

"Heteroaryl" is an aromatic heterocyclic ring. Preferred heteroaryl groups include, but are not limited to, thienyl, furyl, pyrrolyl, pyridinyl, pyrazinyl, oxazolyl, thiazolyl, quinolinyl, pyrimidinyl, and tetrazolyl.

"Alkoxy" s an oxygen atom having a hydrocarbon chain substituent, where the hydrocarbon chain is an alkyl or alkenyl (e.g. —O-alkyl or —O-alkenyl); an alkyl radical attached to the remainder of the molecule by oxygen; as, methoxy. Preferred alkoxy groups include, but are not limited to, methoxy, ethoxy, propoxy, and alkyloxy.

"Hydroxylalkyl" is a substituted hydrocarbon chain which has a hydroxy substituent (e.g. —OH), and may have other substituents. Preferred hydroxyalkyl groups include, but are not limited to, hydroxyethyl, hydroxypropyl, phenylhydroxyalkyl.

"Carboxyalkyl" is a substituted hydrocarbon chain which has a carboxy substituent (e.g. —COOH) and may have other substituents. Preferred carboxyalkyl groups include carboxymethyl, carboxyethyl, and their acids and esters.

"Oxosilane" is an oxygen and silicone repeating unit Si—O—Si—O—, also known in the art as "siloxane."

"Aminoalkyl" is a hydrocarbon chain, (e.g. alkyl) substituted with an amine moiety (e.g. NH-alkyl-), such as dimethylamino alkyl.

"Alkylamino" is an amino moiety having one or two alkyl substituents (e.g. —N-alkyl).

"Alkenylamino" is an amino moiety having one or two alkenyl substituents (e.g. —N-alkenyl).

"Alkynylamino" is an amino moiety having one or two alkynyl substituents (e.g. —N-alkynyl).

"Alkylimino" is an imino moiety having one or two alkyl substituents (e.g. N=alkyl-).

"Arylalkyloxy" is an oxygen atom having an aryl alkyl substituent, e.g. phenylmethoxy or phenylmethyleneoxy

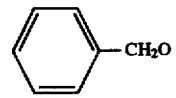

"Heteroarylalkyloxy" is an oxygen atom having a "heteroarylalkyl" substituent, e.g.

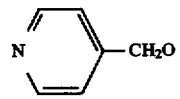

"Arylalkyl" is an alkyl moiety substituted with an aryl group. Preferred arylalkyl groups include benzyl and phenylethyl.

"Heteroarylalkyl" is an alkyl moiety substituted with a heteroaryl group.

"Arylamino" is an amino moiety substituted with an aryl group (e.g. —NH-aryl).

"Aryloxy" is an oxygen atom having an aryl substituent (e.g. —O-aryl).

"Acyl" or "carbonyl" is a moiety formed by removal of the hydroxy from a carboxylic acid (e.g. R—C(=O)—). Preferred alkylacyl groups include, but are not limited to, acetyl, propionyl, and butanoyl.

"Acyloxy" is an oxygen atom having an acyl substituent (e.g. —O-acyl); for example, —O—C(=O)-alkyl.

"Acylamino" is an amino moiety having an acyl substituent (e.g. —N-acyl); for example, —NH—(C=O)-alkyl.

"Benzoxy": The benzoyloxy radical.

"Benzoyl": The aryl radical, $C_6H_5CO$—, derived from benzoic acid.

"Benzoyloxy": e.g. Benzoxy. The radical $C_6H_5COO$—, derived from benzoic acid.

"Carbamate": A salt of carbamic acid; it contains the —$NCO_2$— radical, also known in the art as urethanes or carbamic esters.

"Carboxy": Prefix indicating the acidic carboxyl group.

"Ester": An organic salt formed from an alcohol (base) and an organic acid by elimination of water; functional group derivatives of carboxylic acids are those compounds that are transformed into carboxylic acids by simple hydrolysis. The most common such derivatives are esters, in which the hydroxy group is replaced by an alkoxy group,

"Glycoside": A natural compound of a sugar with another substance, which hydrolyzes a sugar plus a principle: (e.g. coniferin yields glucose plus coniferyl alcohol as the principle; glucosides yield glucose, fructosides yield fructose, galactosides yield galactose, etc.; the cyclic acetal of a carbohydrate.

"Halo", "halogen", or "halide" is a chloro, bromo, fluoro, or iodo atom radical. Chloro, bromo, and fluoro are preferred halides.

"Lactone": Any of a class of inner esters of hydroxy carboxylic acids formed by the loss of a molecule of water from the hydroxy and carboxyl groups of the acids, characterized by the carboxyl-oxy grouping —OCO— in a ring, and classed according to the position of the hydroxy group in the parent acid.

A "pharmaceutically-acceptable" salt is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987, hereby incorporated by reference herein. Preferred cationic salts include the alkali-metal salts (such as sodium and potassium), and alkaline earth metal salts (such as magnesium and calcium). Suitable anionic salts include the halides (such as chloride) salts, as well as the carboxylate (such as maleate) salts. Preferred anionic salts include the maleate salt.

"Salts": Substances produced from the reaction between acids and bases; a compound of a metal (positive) and nonmetal (negative) radical: M. OH (base)+HX (acid)=MX (salt)+$H_2O$ (water).

"Steroid nucleus": Generic name for a family of lipid compounds comprising the sterols, bile acids, cardiac glycosides, saponins, and sex hormones.

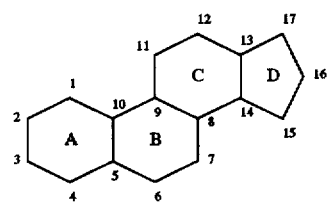

"Substituent": Any atom or group replacing the hydrogen of a parent compound.

"Substitute": To replace one element or radical in a compound by a substituent.

"Substituted": Pertaining to a compound which has undergone substitution.

"Substitution": A reaction in which an atom or group of atoms in a (usually organic) molecule is exchanged for another.

Substituent groups may themselves be substituted. Such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g. aminomethyl, etc.), cyano, halo, carboxy, alkoxyacetyl (e.g. carboethoxy, etc.), thiol, aryl, cycloalkyl, heteroaryl, heterocycloalkyl (e.g., piperidinyl, morpholinyl, piperazinyl, pyrrolidinyl, etc.), imino, thioxo, hydroxyalkyl, aryloxy, arylalkyl, and combinations thereof.

A "monosaccharide" is a single sugar moiety; e.g. hexose, 2-deoxyglucose, 6-deoxyhexose, 2,6-dideoxyhexose, etc., rhamnose, glucose, arabinose, digitoxose, fructose, galactose; rhamnopyranose, hexopyranose, 6-deoxyglucose, 4,6-dideoxyglycopyranose, mannose, cymarose, xylose, lyxose, ribose, digitalose, 4-amino-2,4,6-trideoxylyxohexopyranose, 4-amino-4,6, dideoxyglucopyranose, 2,3-dideoxyrhamnopyranose, 4-methoxy 4,6-dideoxyrhamnopyranose.

An "oligosaccharide" is a sugar having 2-8 monosaccharide sugar residues, preferably 2-3. The last monosaccharide residue of the oligosaccharide is known as the "terminal" oligosaccharide residue.

The "monosaccharide" or "oligosaccharide" residue can be graphically depicted in either a ring or a chair configuration. For example, glucose (a monosaccharide) can be represented accordingly:

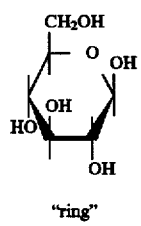

"ring"

-continued

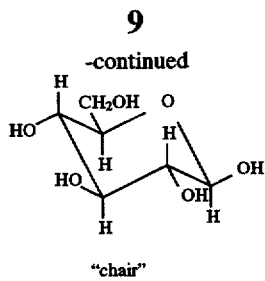

"chair"

DETAILED DESCRIPTION OF THE INVENTION

The present invention encompasses certain deoxy or oxygen-substituted sugar-containing 14-aminosteroid compounds, methods for their manufacture, pharmaceutical compositions thereof, and a method of treatment utilizing said novel compounds and compositions thereof for treating congestive heart failure in humans or other mammals. Specific compounds and compositions to be used in the invention must, accordingly, be pharmaceutically-acceptable. As used herein, such a "pharmaceutically-acceptable" component is one that is suitable for use with humans and/or other mammals without undue adverse side effects (such as toxicity, irritation, and allergic response), commensurate with a reasonable benefit/risk ratio.

ACTIVE MATERIALS

Deoxy or oxygen-substituted sugar-containing 14-aminosteroid compounds and the pharmaceutically-acceptable acid salts or esters thereof of the general formula:

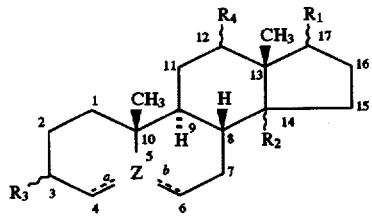

wherein a) $R_1$ is
  (i) $COOR_5$, where
    $R_5$ is a 1–6 carbon lower alkyl group; a 1–6 carbon lower alkyl group substituted by an amino group; an arylalkyl or a heteroarylalkyl group or a carbocyclic ring or
  (ii) $CHR_6OH$, where
    $R_6$ is a hydrogen atom or a 1–6 carbon lower alkyl group; or
  (iii) $COR'''$ where $R'''$ is hydrogen; 1–6 carbon lower alkyl; 1–6 carbon lower alkyl substituted amino; amino or dialkylamino;

b) $R_2$ is $-NR_7R_8$, where $R_7$ and $R_8$, which may be the same or different, are hydrogen atoms or a 1–6 carbon lower alkyl group;

c) $R_3$ is
  (i) a deoxy or oxygen-substituted monosaccharide sugar residue,

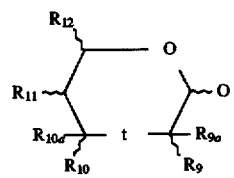

wherein $R_{9a}$, $R_9$, $R_{10}$, and $R_{10a}$, which may be the same or different, are 1–6 carbon lower alkyl; hydrogen; hydroxy; fluorine; alkoxy; acetoxy; arylalkyloxy; heteroarylalkyloxy or benzoxy; $R_{11}$ is 1–6 carbon lower alkyl; hydrogen; hydroxy; fluorine; benzoxy; heteroarylalkyloxy; arylalkyloxy; acetoxy or alkoxy; wherein further when $R_5$ is a 1–6 carbon lower alkyl; either $R_9$, $R_{10}$, or $R_{11}$ cannot be hydroxy or acetoxy; further provided that when $R_{9a}$ is hydrogen and $R_{10a}$ is hydrogen and $R_9$ is hydrogen; hydroxy or acetoxy; and $R_{11}$ is hydroxy; acetoxy or alkoxy; $R_{10}$ cannot be hydroxy or acetoxy; and $R_{12}$ is methyl; acetoxymethyl or hydroxymethyl; t can be a single or double bond or (ii) a deoxy or oxygen-substituted monosaccharide sugar residue,

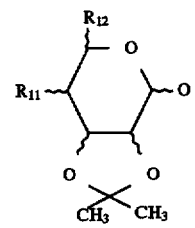

wherein $R_{11}$ is arylalkyloxy; heteroarylalkyloxy or 1–6 carbon lower alkyl substituted oxosilane and $R_{12}$ is methyl; and d) $R_4$ is
  (i) OH, or
  (ii) H, or
  (iii) $OR_{13}$, where $R_{13}$ is a monosaccharide sugar residue; acetoxy; benzoxy; arylalkyl or heteroarylalkyl or e) Z is
  (i) —CH—, where a and b are single bonds, or
  (ii) =C, where either a or b is a double bond.

The "~" symbol, as used herein, indicates that the stereochemistry is undefined, and that the substituents on the steroid nucleus can be in either the α or β configuration. The preferred stereochemistry is the β configuration at positions 3, 12, 14 and 17 on the steroid nucleus. The deoxy or oxygen-substituted monosaccharide sugar residues of the present invention can be linked to the 3-position on the steroid nucleus in either the α or β configuration. Further, one skilled in the art of carbohydrate chemistry understands that the configuration of the substituents on a given sugar residue is defined by the specific named sugar.

The Steroid Nucleus

The novel deoxy or oxygen-substituted sugar-containing 14-aminosteroid compounds of the present invention are comprised of a steroid nucleus wherein said steroid nucleus is variously substituted.

THE SUBSTITUENTS ON THE STEROID NUCLEUS

The $R_1$ Substituents

The $R_1$ substituent is at the 17-position on the steroid nucleus. There are three (3) possible $R_1$ substituents. $R_1$ can be $COOR_5$ where $R_5$ is hydrogen, a 1–6 carbon lower alkyl group, a 2–6 carbon lower alkyl group substituted by an amino group, or an arylalkyl; or heteroarylalkyl group or a carbocyclic ring. Preferred $R_5$ substituents are 1–6 carbon lower alkyl, arylalkyl or a carbocycle, the more preferred $R_5$ is a 1–6 carbon lower alkyl and the most preferred $R_5$ is methyl; thus, $R_1$ is a carboxylic acid ester ($COOCH_3$).

$R_1$ can also be $CHR_6OH$ where $R_6$ is a hydrogen atom or a 1–6 carbon lower alkyl group; the preferred $R_6$ is H; thus, $R_1$ is $CH_2OH$.

Finally, $R_1$ can be $COR'''$, where $R'''$ is hydrogen, 1–6 carbon lower alkyl, methylamino, amino or dialkylamino; the most preferred $R'''$ is methylamino; thus, $R_1$ is $CONHCH_3$.

The most preferred $R_1$ substituent is $COOR_5$, where $R_5$ is methyl and; thus, $R_1$ is a carboxylic acid methyl ester (e.g. $COOCH_3$).

The $R_2$ Substituent

The $R_2$ substituent is at the 14-position on the steroid nucleus. There is one (1) $R_2$ substituent. $R_2$ is —$NR_7R_8$ where $R_7$ and $R_8$, which may be the same or different, are hydrogen atoms or lower alkyl group containing 1 to 6 carbon atoms. Preferably $R_7$ and $R_8$ are H and, thus, $R_2$ is $NH_2$.

The $R_3$ Substituents

The $R_3$ substituent is at the 3-position on the steroid nucleus. There are two (2) $R_3$ substituents. $R_3$ can be a deoxy or oxygen-substituted sugar-containing residue having the following structure:

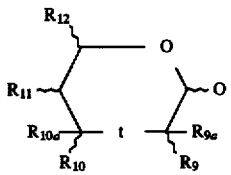

$R_{9a}$, $R_9$, $R_{10}$, and $R_{10a}$, which may be the same or different, are 1–6 carbon lower alkyl; hydrogen; hydroxy; fluorine; alkoxy; acetoxy; arylalkyloxy; heteroarylalkyloxy or benzoxy; $R_{11}$ is 1–6 carbon lower alkyl; hydrogen; hydroxy; fluorine; benzoxy; arylalkyloxy; heteroarylalkyloxy; acetoxy or alkoxy; wherein further when $R_5$ is 1–6 carbon lower alkyl, either $R_9$, $R_{10}$, or $R_{11}$ cannot be hydroxy or acetoxy; and further provided that when $R_{9a}$ is hydrogen and $R_{10a}$ is hydrogen and $R_9$ is hydrogen, hydroxy or acetoxy and $R_{11}$ is hydroxy, acetoxy or alkoxy, $R_{10}$ cannot be hydroxy or acetoxy; and $R_{12}$ is methyl; acetoxymethyl or hydroxymethyl; t can be a single or double bond.

Accordingly, in the compounds of the present invention, when $R_1$ is $COOR_5$, and $R_5$ is a 1–6 carbon lower alkyl, and $COOR_5$ is a carboxylic acid ester, $R_9$ and $R_{9a}$ and $R_{10a}$ can be hydrogen but either $R_{10}$ or $R_{11}$ cannot be hydroxy or acetoxy; $R_{11}$ cannot be alkoxy. $R_{10}$ is selected from hydrogen, 1–6 carbon lower alkyl, fluorine, alkoxy, arylalkyloxy, heteroarylalkyloxy or benzoxy. $R_{11}$ is selected from hydrogen, 1–6 carbon lower alkyl, fluorine, arylalkyloxy, heteroarylalkyloxy or benzoxy. Thus, when $R_9$ and $R_{9a}$ and $R_{10a}$ are hydrogen, $R_{10}$ can be hydroxy and $R_{11}$ is selected from 1–6 carbon lower alkyl, fluorine, hydrogen, arylalkyloxy, heteroarylalkyloxy or benzoxy. Further, when $R_9$ and $R_{9a}$ and $R_{10a}$ are hydrogen, $R_{10}$ can be acetoxy and $R_{11}$ is selected from 1–6 carbon lower alkyl, fluorine, hydrogen, arylalkyloxy, heteroarylalkyloxy or benzoxy. Also, when $R_9$ and $R_{9a}$ and $R_{10a}$ are hydrogen, $R_{11}$ can be hydroxy and $R_{10}$ is selected from hydrogen, 1–6 carbon lower alkyl, fluorine, alkoxy, arylalkyloxy, heteroarylalkyloxy or benzoxy. When $R_9$ and $R_{9a}$ and $R_{10a}$ are hydrogen, $R_{11}$ can be acetoxy and $R_{10}$ is selected from hydrogen, 1–6 carbon lower alkyl, fluorine, alkoxy, arylalkyloxy, heteroarylalkyloxy or benzoxy.

Additionally, when $R_1$ is $COOR_5$, and $R_5$ is a 1–6 carbon lower alkyl, and $COOR_5$ is a carboxylic acid ester, $R_9$ can be hydroxy, $R_{9a}$ can be hydrogen, $R_{10a}$ can be hydrogen, but either $R_{10}$ or $R_{11}$ cannot be hydroxy or acetoxy; and $R_{11}$ cannot be alkoxy. $R_{10}$ is selected from hydrogen, 1–6 carbon lower alkyl, fluorine, alkoxy, arylalkyloxy, heteroarylalkyloxy or benzoxy. $R_{11}$ is selected from hydrogen, 1–6 carbon lower alkyl, fluorine, arylalkyloxy, heteroarylalkyloxy or benzoxy. Thus, when $R_9$ is hydroxy and $R_{9a}$ is hydrogen and $R_{10a}$ is hydrogen, $R_{10}$ can be OH and $R_{11}$ is selected from hydrogen, 1–6 carbon lower alkyl, fluorine, arylalkyloxy, heteroarylalkyloxy or benzoxy. Further, when $R_9$ is hydroxy and $R_{9a}$ is hydrogen and $R_{10a}$ is hydrogen, $R_{10}$ can be acetoxy and $R_{11}$ is selected from hydrogen, 1–6 carbon lower alkyl, fluorine, arylalkyloxy, heteroarylalkyloxy or benzoxy. Also, when $R_9$ is hydroxy, and $R_{9a}$ is hydrogen and $R_{10a}$ is hydrogen, $R_{11}$ can be hydroxy and $R_{10}$ is selected from hydrogen, 1–6 carbon lower alkyl, fluorine, alkoxy, arylalkyloxy, heteroarylalkyloxy or benzoxy. When $R_9$ is hydroxy and $R_{9a}$ is hydrogen and $R_{10a}$ is a hydrogen, $R_{11}$ can be acetoxy and $R_{10}$ is selected from hydrogen, 1–6 carbon lower alkyl, fluorine, alkoxy, arylalkyloxy, heteroarylalkyloxy or benzoxy.

Further, when $R_1$ is $COOR_5$, and $R_5$ is a 1–6 carbon lower alkyl, and $COOR_5$ is a carboxylic acid ester, $R_9$ can be acetoxy and $R_{9a}$ can be hydrogen and $R_{10a}$ can be hydrogen, but either $R_{10}$ or $R_{11}$ cannot be hydroxy or acetoxy; and $R_{11}$ cannot be alkoxy. $R_{10}$ is selected from hydrogen, 14 carbon lower alkyl, fluorine, alkoxy, arylalkyloxy, heteroarylalkyloxy or benzoxy. $R_{11}$ is selected from hydrogen, 1–6 carbon lower alkyl, fluorine, arylalkyloxy, heteroarylalkyloxy or benzoxy. Thus, when $R_9$ is acetoxy and $R_{9a}$ is hydrogen and $R_{10a}$ is hydrogen, $R_{10}$ can be hydroxy and $R_{11}$ is selected from 1–6 carbon lower alkyl, fluorine, hydrogen, arylalkyloxy, heteroarylalkyloxy or benzoxy. Further, when $R_9$ is acetoxy and $R_{9a}$ is hydrogen and $R_{10a}$ is hydrogen, $R_{10}$ can be acetoxy and $R_{11}$ is selected from 1–6 carbon lower alkyl, fluorine, hydrogen, arylalkyloxy, heteroarylalkyloxy or benzoxy. Also, when $R_9$ is acetoxy and $R_{9a}$ is hydrogen and $R_{10a}$ is hydrogen, $R_{11}$ can be hydroxy and $R_{10}$ is selected from 1–6 carbon lower alkyl, fluorine, alkoxy, hydrogen, arylalkyloxy, heteroarylalkyloxy or benzoxy. Further, when $R_9$ is acetoxy, and $R_{9a}$ is hydrogen and $R_{10a}$ is hydrogen. $R_{11}$ can be acetoxy and $R_{10}$ is selected from hydrogen, 1–6 carbon lower alkyl, fluorine, alkoxy, arylalkyloxy, heteroarylalkyloxy or benzoxy.

Preferred $R_9$ substituents are hydrogen, fluorine, hydroxy, 1–6 carbon lower alkyl or acetoxy. The most preferred $R_9$ substituents are hydrogen, hydroxy and fluorine.

Preferred $R_{9a}$ substituents are hydrogen, fluorine, hydroxy and a 1–6 carbon lower alkyl, preferably methyl and fluorine.

Preferred $R_{10}$ substituents are hydrogen, fluorine, hydroxy, arylalkyloxy, heteroarylalkyloxy, acetoxy or methyl. The most preferred $R_{10}$ substituents are hydrogen, methyl and fluorine.

Preferred $R_{10a}$ substituents are hydrogen, fluorine, hydroxy, and a 1–6 carbon lower alkyl, preferably methyl. The most preferred $R_{10a}$ substituents are hydrogen, methyl and fluorine.

Preferred $R_{11}$ substituents are hydroxy, arylalkyloxy, heteroarylalkyloxy and acetoxy. The most preferred $R_{11}$ substituents are hydroxy and acetoxy.

Preferred $R_{12}$ substituents are methyl, acetoxymethyl and hydroxymethyl. The most preferred $R_{12}$ substituent is methyl.

In a particularly preferred compound of the present invention, $R_{9a}$ is hydrogen; $R_9$ is hydroxy; $R_{10}$ is hydrogen; $R_{10a}$ is hydrogen; and $R_{11}$ is hydroxy.

$R_3$ can also be a deoxy or oxygen-substituted sugar-containing residue having the following structure:

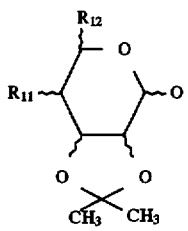

wherein $R_{11}$ is arylalkyloxy, heteroarylalkyloxy or 1–6 carbon lower alkyl substituted oxosilane and $R_{12}$ is methyl.

The $R_4$ Substituents

The $R_4$ substituent is at the 12-position on the steroid nucleus. $R_4$ can be hydroxy (OH), hydrogen (H), or $OR_{13}$, where $R_{13}$ is a monosaccharide sugar residue; acetoxy, benzoxy or arylalkyl or heteroarylalkyl. The preferred $R_4$ substituents are H or $OR_{13}$, where $R_{13}$ is a monosaccharide residue. Said monosaccharide residue is selected from hexose, 2-deoxyglucose, 6-deoxyhexose, 2,6-dideoxyhexose, rhamnose, a glucose and arabinose, a digitoxose, a fructose, a galactose, rhamnopyranose, hexopyranose, 6-deoxyglucose, 4,6-dideoxyglycopyranose, mannose, cymarose, xylose, lyxose, ribose, digitalose, glucosamine, 4-amino-2,4,6-trideoxylyxohexopyranose, 4-amino-4,6-dideoxyglycopyranose, 2,3-didexoyrhamnopyranose, 4-methoxy 4,6-dideoxyrhanmopyranose, preferably the β-D or α-L anomers thereof.

The most preferred $R_4$ substituent is H.

Z

Z is —CH—, where a and b are single bonds, or ═C, where either a or b is a double bond. The preferred Z is —CH where a and b are single bonds.

Preferred deoxy and oxygen-substituted sugar-containing 14-aminosteroid compounds of the present invention are:

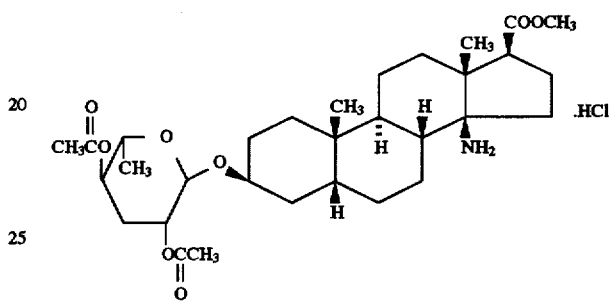

(3β,5β,14β,17β)-14-Amino-3-[(2,4-di-O-acetyl-3,6-dideoxy-α-L-mannopyranosyl)oxy]androstane-17-carboxylic acid, methyl ester hydrochloride

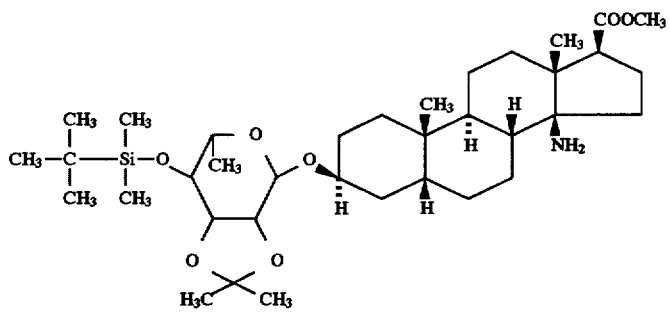

(3β,5β,14β,17β)-14-Amino-3-[(6-Deoxy-2,3-O-(1-methylethylidene)-4-O-[(1,1-dimethylethyl)dimethylsilyl]-α-L-mannopyranosyl)oxy]androstane-17-carboxylic acid, methyl ester

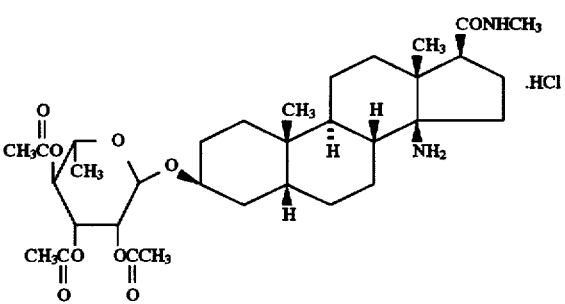

(3β,5β,14β,17β)-14-Amino-3-[(6-deoxy-2,3,4-tri-O-acetyl-α-L-mannopyranosyl) oxy]-N-methylandrostane-17-carboxamide hydrochloride

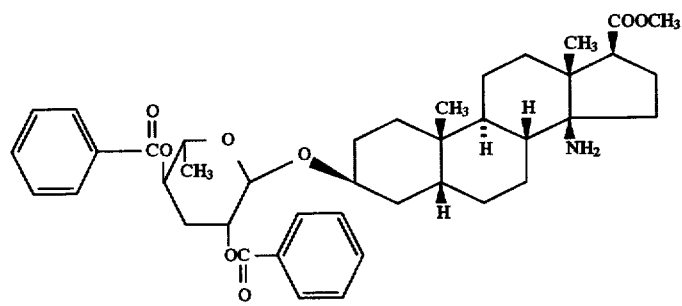

(3β,5β,14β,17β)-14-Amino-[(2,4-di-O-benzoyl-3,6-dideoxy-α-L-mannopyranosyl)oxy]androstane-17-carboxylic acid, methyl ester

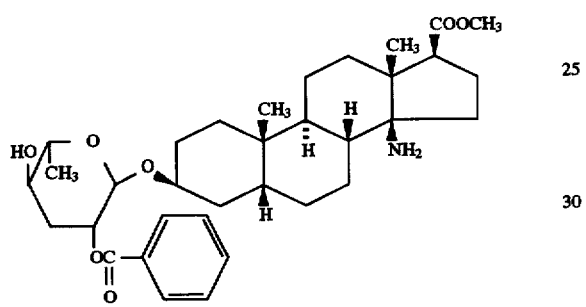

(3β,5β,14β,17β)-14-Amino-[(2-O-benzoyl-3,6-dideoxy-α-L-mannopyranosyl)oxy]androstane-17-carboxylic acid, methyl ester

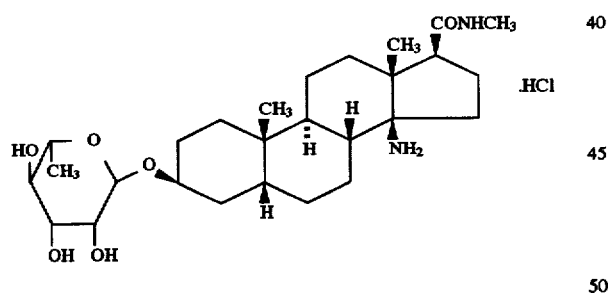

(3β,5β,14β,17β]-14-Amino-3-[(6-deoxy-α-L-mannopyranosyl)oxy]-N-methylandrostane-17-carboxamide hydrochloride

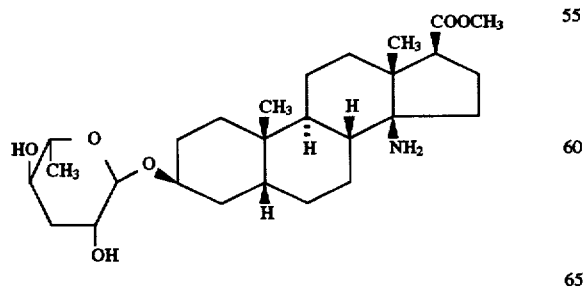

(3β,5β,14β,17β)-14-Amino-3-[(3,6-dideoxy-α-L-mannopyranosyl) oxy]androstane-17-carboxylic acid, methyl ester

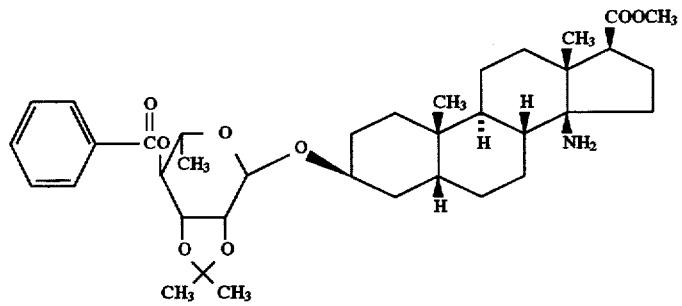

(3β,5β,14β,17β)-14-Amino-3-[[4-O-benzoyl-6-deoxy-2,3-O-(1-methylethylidene)-α-L-mannopyranosyl]oxy] androstane-17-carboxylic acid, methyl ester

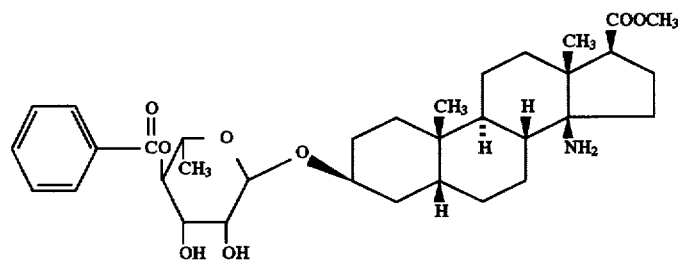

(3β,5β,14β,17β)-14-Amino-3-[(4-O-benzoyl-6-deoxy-α-L-mannopyranosyl)oxy]androstane-17-carboxylic acid, methyl ester

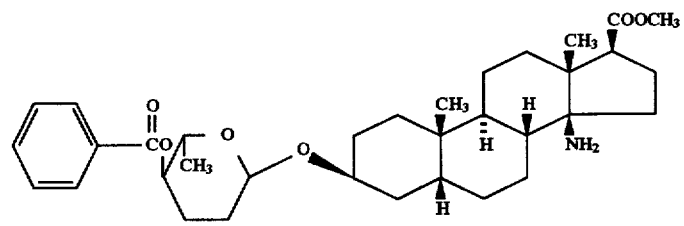

(3β,5β,14β,17β)-14-Amino-3-[(4-O-benzoyl-2,3,6-trideoxy-β-L-mannopyranosyl)oxy]androstane-17-carboxylic acid, methyl ester

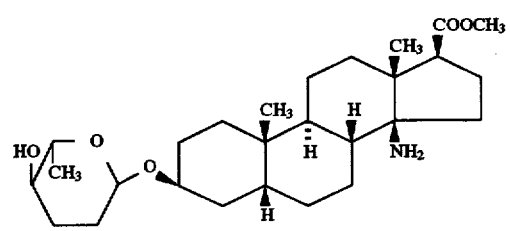

(3β,5β,14β,17β)-14-Amino-3-[(2,3,6-trideoxy-β-L-mannopyranosyl)oxy]androstane-17-carboxylic acid, methyl ester

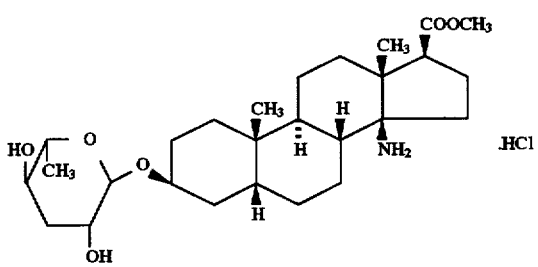

(3β,5β,14β,17β)-14-Amino-3-[(3,6-dideoxy-α-L-mannopyranosyl)oxy] androstane-17-carboxylic acid, methyl ester hydrochloride

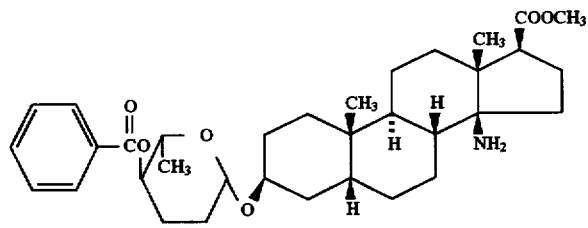

(3β,5β,14β,17β)-14-Amino-3-[(4-O-benzoyl-2,3,6-trideoxy-α-L-mannopyranosyl)oxy]androstane-17-carboxylic acid, methyl ester

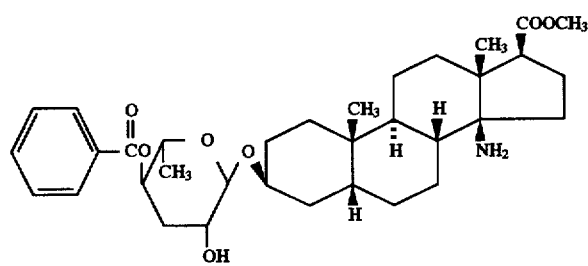

(3β,5β,14β,17β)-14-Amino-3-[(4-O-benzoyl-3,6-dideoxy-α-L-mannopyranosyl)oxy]androstane-17-carboxylic acid, methyl ester

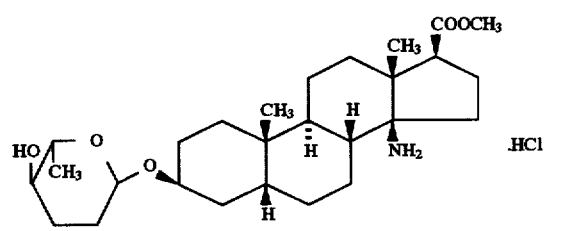

(3β,5β,14β,17β)-14-Amino -3-[(2,3,6-trideoxy-α-L-mannopyranosyl)oxy] androstane-17-carboxylic acid, methyl ester hydrochloride

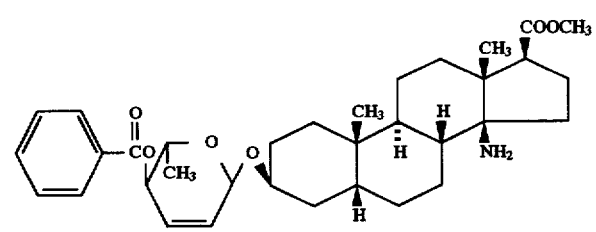

(3β,5β,14β,17β)-14-Amino-3-[(4-O-benzoyl-2,3-didehydro-2,3,6-trideoxy-α-L-mannopyranosyl)oxy]androstane-17-carboxylic acid, methyl ester

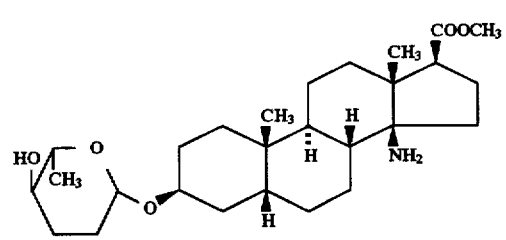

(3β,5β,14β,17β)-14-Amino-3-[(2,3,6-trideoxy-α-L-mannopyranosyl)oxy]androstane-17-carboxylic acid, methyl ester

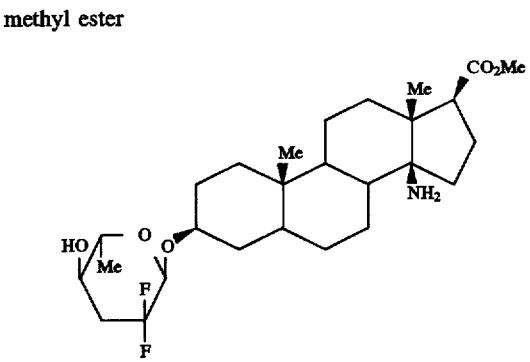

(3β, 5β, 14β, 17β)-14-Amino-3-[(2',3',6'-trideoxy-2',2'-difluoro-α-L-mannopyranosyl)-oxy]-androstane-17-carboxylic acid methyl ester

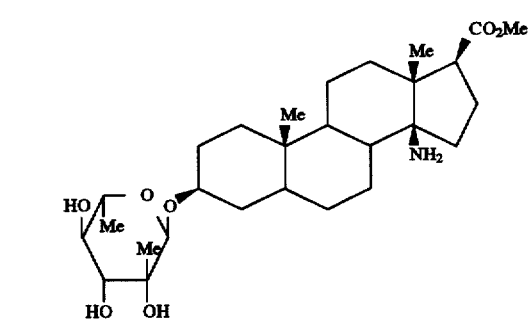

(3β, 5β, 14β, 17β)-14-Amino-3-[(6'-deoxy-2'-methyl-α-L-mannopyranosyl)-oxy]androstane-17-carboxylic acid methyl ester

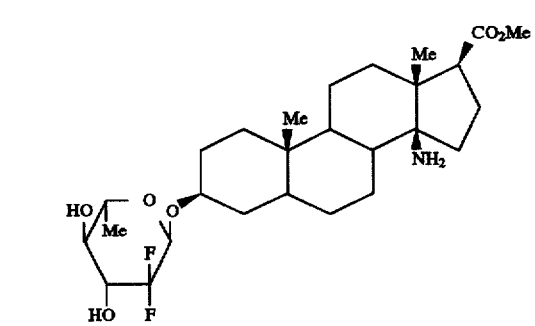

(3β, 5β, 14β, 17β)-14-Amino-3-[(2', 6'-dideoxy-2', 2'-difluoro-α-L-mannopyranosyl)-oxy]-androstane-17-carboxylic acid methyl ester

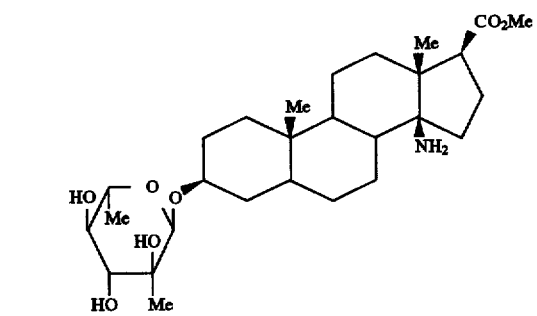

(3β, 5β, 14β, 17β)-14-Amino-3-[(6'-deoxy-2'-C-methyl-α-L-glucopyranosyl)-oxy]-androstane-17-carboxylic acid methyl ester

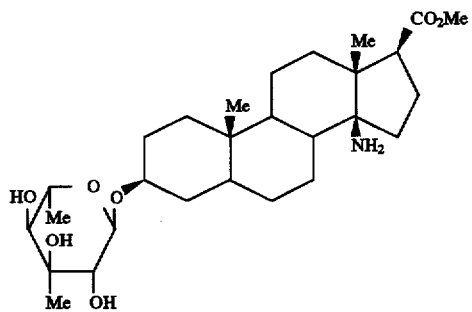

(3β, 5β, 14β, 17β)-14-Amino-3-[(6'-deoxy-3'-C-methyl-α-L-altropyranosyl)-oxy]-androstane-17-carboxylic acid methyl ester

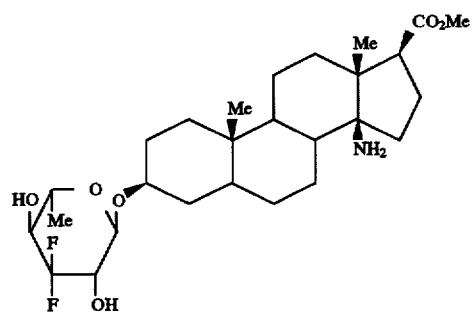

(3β, 5β, 14β, 17β)-14-Amino-3-[(6'-deoxy-3'-3'-difluoro-α-L-mannopyranosyl)-oxy]-androstane-17-carboxylic acid methyl ester

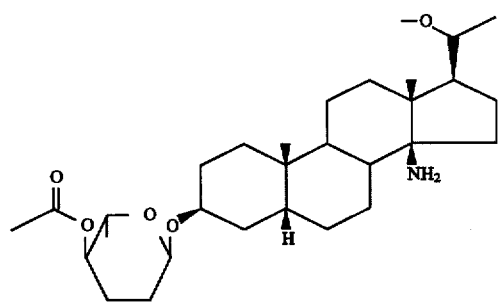

14β-amino-20β-methoxy-3β-[(2',3'-deoxy-4'-acetoxy)-α-(L)-rhamnopyranosyl-oxy]-5β,17α(H)-pregnane

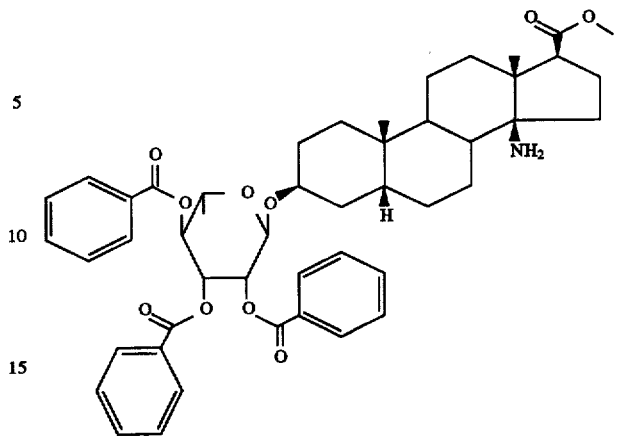

14β-amino-3β-[(tri-2',3',4'-O-benzoyl)-α-(L)-rhamnopyranosyloxy]-5β-androstane-17β-carboxylic acid, methyl ester

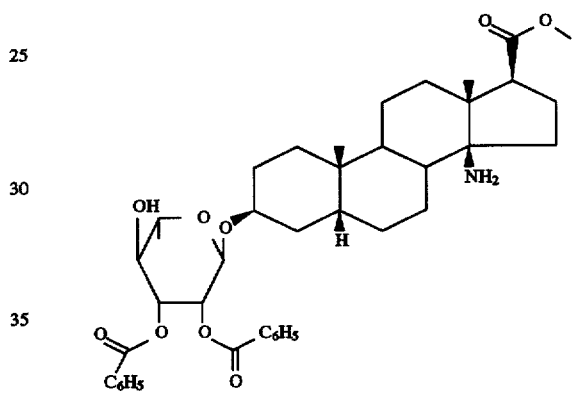

14β-amino-3β-[(di-2',3'-O-benzoyl)-α(L)-rhamnopyranosyloxy]-5β-androstane-17-carboxylic acid, methyl ester

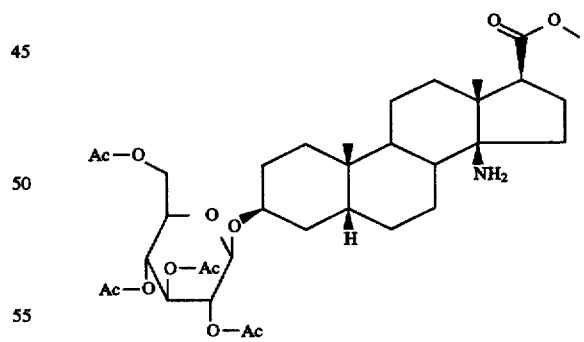

14β-amino-3β-[tetra-O-acetyl)-β-(D)-glucopyranosyloxy]-5β-androstane-17β-carboxylic acid, methyl ester

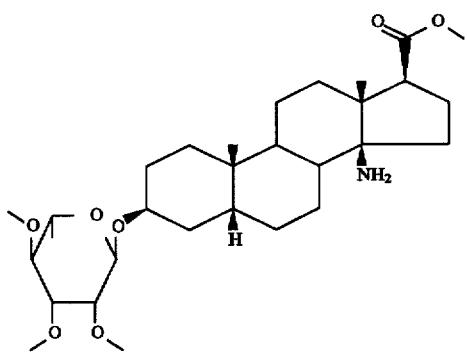

14β-amino-3β-[(2',3',4'-tri-O-methyl)-α-(L)-rhamnopyranosyloxy]-5β-androstane-17β-carboxylic acid, methyl ester

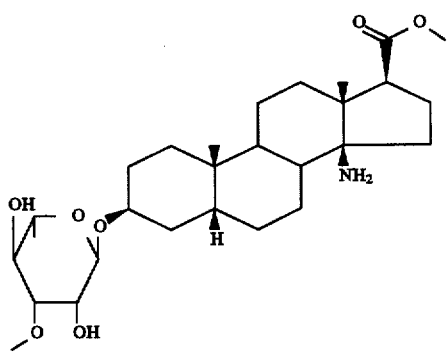

14β-amino-3β-[(3'-O-methyl)-α-(L)-rhamnopyranosyloxy]-5β-androstane-17β-carboxylic acid, methyl ester

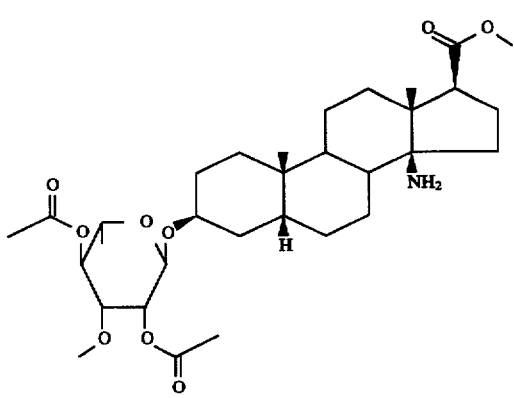

14β-amino-3β-[(di-2',4'-O-acetyl-3'-O-methyl)-α-(L)-rhamnopyranosyloxy]-5β-androstane-17β-carboxylic acid, methyl ester

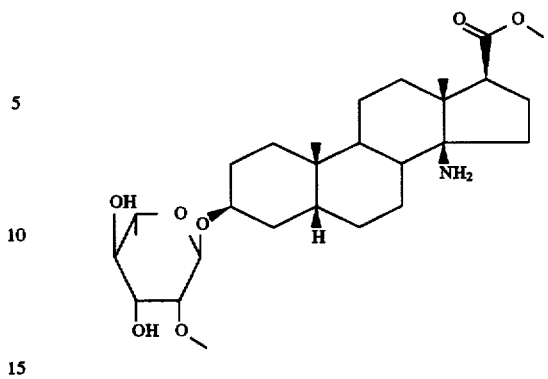

14β-amino-3β-[(2'-O-methyl)-α-(L)-rhamnopyranosyloxy]-5β-androstane-17β-carboxylic acid, methyl ester

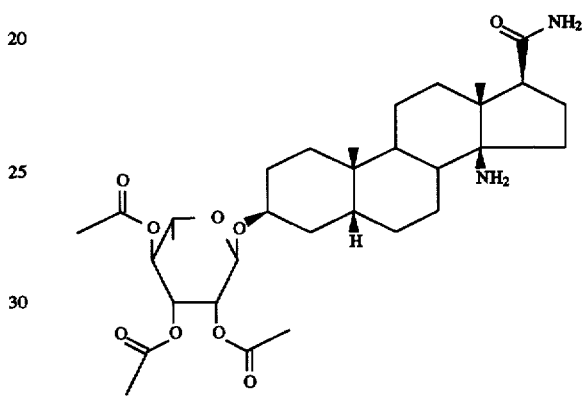

14βamino-3β-[(tri-2',3'-4'-O-acetyl)-α-(L)-rhamnopyranosyloxy]-5β-androstane-17α(H)-carboxamide In making the preferred compounds of the invention, a preferred starting material and/or intermediate is 3,6-dideoxy-L-erythro-hex-2-enonic acid, δ-lactone, 2,4-O-dibenzoate, and has the following structure:

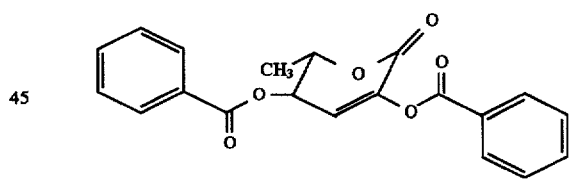

A preferred synthesis of said starting material/intermediate compound, using the following general reaction scheme, is described in Example 24, Part A. Generally, 3,6-dideoxy-L-erythro-hex-2-enonic acid, δ-lactone, 2,4-O-dibenzoate is synthesized by first preparing the compound, 6-deoxy-α-L-mannopyranosyl bromide, 2,3,4-tri-O-benzoate, using the procedure described by Ness, R. K., Fletcher, H. G.; Hudson, C. S., *J. Am. Chem. Soc.*, Vol. 73, p. 296 (1951) and by Allard, P.; Dinh, T. H.; Boujette, C.; Igolen, J., *J. Med. Chem.*, 1981, Vol. 24, p. 1291). Then, said compound is added to DMSO and a suitable base at temperatures of 50° C. to 150° C., preferably 60°–80° C., most preferably 70° C., for 5 minutes to about 30 minutes, preferably 15 mutes to about 20 minutes.

Said suitable base can be chosen from tertiary amines, pyridine, collidine, amidine bases and heteroaryl amine bases (including, but not limited to, pyridine and collidine), preferably triethylamine (Et₃N). While DMSO can be used alone with the base, performing as both a solvent and a reactant, it could be used only as a reactant (with quantity adjusted accordingly) and combined with a suitable solvent. Said suitable solvent includes chlorinated solvents, aromatic hydrocarbons, esters, and ethers.

After the reaction is complete, said reaction mixture may be poured over ice water, and then purified and extracted, using methods known by those skilled in the art. While the preferred method of synthesis for this starting material is defined in Example 24, given the general reaction described hereinabove, one skilled in the art could use various solvents, bases, extractions and purification procedures to synthesize said starting material. It is preferable that the reaction be anhydrous.

In addition to the general synthesis scheme described hereinabove, and to the preferred synthesis embodying that scheme in Example 24, the said preferred starting material, 3,6-dideoxy-L-erythro-hex-2-enonic acid, δ-lactone, 2,4-O-dibenzoate can also be synthesized using the general procedure set forth hereinbelow; a preferred embodiment of the following general scheme is set forth in Example 25.

Generally, α-L-6-deoxy-mannopyranose, monohydrate is combined with a suitable solvlent, including, but not limited to, DMF and acetonitrile. Next, a suitable oxidant, including, but not limited to, benzoyl peroxide, is added to the mixture, along with a suitable metal chloride or bromide, selected from the group consisting of, but not limited to, lithium bromide, lithium chloride, nickel bromide, and nickel chloride. The resulting reaction mixture is stirred at temperatures of 20° C. to 100° C., preferably 20°–60° C., until the reaction is complete.

Next, a suitable base, selected from the group consisting of tertiary amines, amidine bases, and heteroaryl amine bases (including but not limited to, pyridine and collidine), preferably triethylamine (Et₃N) is added to the reaction mixture, followed by the addition of benzoyl chloride. The resulting reaction mixture is stirred at 0° C. to 100° C., preferably 20°–60° C., until the reaction is complete. Water is then added to the reaction mixture, and the product is extracted using methods available to those skilled in the art. Suitable solvents including, but not limited to, aromatic hydrocarbons, esters, and ethers. The extracts are purified and crystallized, using methods readily available to one skilled in the art. The preferred synthesis set forth in Example 25 can be varied using different solvents, bases, and oxidants readily available to one of skill in the art, using the general reaction procedure as described above.

METHODS OF MANUFACTURE

The following non-limiting examples are illustrative of the methods of manufacture for the compounds of the present invention.

Example 1

Synthesis of (3β, 5β, 14β, 17β)-14-Amino-3-[(2', 3', 6'-trideoxy-4'-O-benzoyl-α-L-mannopyranosyl)-oxy]-androstane-17-carboxylic acid methyl ester

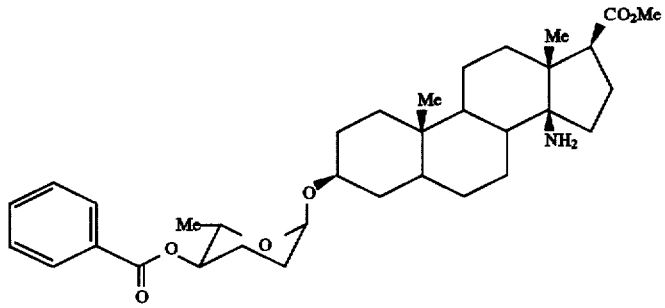

Preparation of methyl 6-deoxy-2,3-O-(1-methylethylidene)-α-L-mannopyranoside, 4-benzoate To a solution of methyl 6-deoxy-2,3-O-(1-methylethylidene)-α-mannopyranoside (6.0 g, 27.5 mmol) in CH₂Cl₂ (50 mL) at 0° C. under nitrogen is added dry pyridine (3 mL). See, Evans, M. E.; Parrish, F. W.; Long, L. Carbohydr. Res. 1967, 3, 453, incorporated by reference herein. With stirring for 5 min, benzoyl chloride (9.5 mL, 82.5 mmol) is added dropwise at 0° C. The reaction mixture is allowed to warm up to room temperature over 30 min and is stirred at ambient temperature for 24 h. The resulting solution is diluted with CH₂Cl₂ (100 mL), washed with H₂O and brine, and dried. Evaporation yields a crude product which is crystallized from hexane/ethyl acetate (3:1) to furnish methyl 6-deoxy-2,3-O-(1-methylethylidene)-α-L-mannopyranoside, 4-benzoate (6.1 g, 78%) as a white solid.

Preparation of methyl 6-deoxy-α-L-mannopyranoside, 4-benzoate

To a solution of methyl 6-deoxy-2,3-O-(1-methylethylidene)-α-L-mannopyranoside, 4-benzoate (6.1 g, 18.9 mmol) in MeOH (190 mL) is added HCl (aq) (3N, 3 mL) at ambient temperature. The resulting mixture is stirred for 6 h. Removal of the solvent yields a semi-solid residue which is crystallized in hexane/ethyl acetate. Recrystallization in the same solvent system yields methyl 6-deoxy-α-L-mannopyranoside, 4-benzoate, (3.2 g, 60%) as a white solid.

An alternative reaction condition is as follows:

To an aqueous methanolic solution of methyl 6-deoxy-2, 3-O-(1-methylethylidene)-α-L-mannopyranoside, 4-benzoate (conc. 0.1M) is added p-TsOH (10 mol %). The resulting mixture is warmed up to 60° C. for 12 h. Evaporation of the solvent yields a residue. The residue is dissolved in CH₂Cl₂, washed with 5% NaHCO₃ (aq), H₂O and brine, and dried. The residue, after removal of the solvent, is crystallized from hexane/ethyl acetate to yield methyl 6-deoxy-α-L-mannopyranoside, 4-benzoate as a white solid.

Preparation of methyl 2, 3, 6-trideoxy-2,3-dehydromannopyranoside 4-benzoate

To a mixture of methyl 6-deoxy-α-L-mannopyranoside, 4-benzoate (10 g, 35.5 mmol), triphenylphosphine (39 g, 149 mmol), triiodoimidazole (26.4 g, 26 mmol), imidazole (5.1 g, 75 mmol and Bu₄NI (12.5 g, 34 mmol) in toluene (850 mL) is stirred at reflux for 2 h. The solution turns to a red-brown color from the I₂ produced. Toluene (150 mL) is added to the reaction mixture which is then poured into stirred NaHCO₃ aqeuous (5%, 800 mL). The remaining residue is dissolved in acetone and poured into the aqueous phase. The resulting mixture is stirred for 5 min. and is separated. The organic layer is washed twice with Na₂S₂O₃ aqueous (5%, 100 mL), twice with NaHCO₃ aqueous (5%, 100 mL), twice with H₂O (100 mL) and dried over anhydrous MgSO₄. Removal of the solvent yields a light yellow crude product. Purification by chromatography (elution with hexane/ethyl acetate in gradient from 50:1 to 50:3.5) gives a pure compound, methyl 2, 3, 6-trideoxy-2, 3-dehydromannopyranoside 4-benzoate (5.1 g, 58%) as a colorless liquid.

Preparation of methyl 6-deoxy-2, 3-dideoxymannopyranoside 4-benzoate

A suspended solution of methyl 2, 3, 6-trideoxy-2, 3-dehydromannopyranoside 4-benzoate (3.2 g, 12.9 mmol) and Raney nickel (excess, washed with H₂O and i-PrOH) in i-PrOH (120 mL) is shaken under H₂ atmosphere (40 psi) for 6 h. The resulting mixture is filtered and concentrated at reduced pressure to yield a colorless liquid product, methyl 2, 3, 6-trideoxymannopyranoside 4-benzoate (3.2 g, 99%).

Preparation of 2, 3, 6-trideoxy-4-benzoyl-1-chloro-β-L-mannopyranose

To a magnetically stirred solution of methyl 2, 3, 6-trideoxymannopyranoside 4-benzoate (4.0 g, 16.0 mmol) in dry CH₂Cl₂ (160 mL) at −70° C. under nitrogen is added dropwise BCl₃ (1.0M in CH₂Cl₂, 20 mL). After complete consumption of the starting material (30 min), NaHCO₃ aqueous (2%, 30 mL) is poured into the mixture at low temperature (the aqueous was initially frozen). The separated organic layer is dried with Na₂SO₄, filtered, then further dried with molecular sieve 4 Å. This solution is directly used for next reaction step. A small portion of the solution is evaporated under vacuum to yield a light yellow liquid product, 2, 3, 6-trideoxy-4-benzoyl-1-chloro-β-L-mannopyranose.

Preparation of (3β, 5β, 14β, 17β)-14-amino-3-[(2', 3', 6'-trideoxy-4-benzoyl-α-L-mannopyranosyl)-oxy]-androstane-17-carboxylic acid methyl ester To a magnetically stirred suspended solution of aglycone, (3β, 5β, 14β, 17β)-14-amino-3-hydroxy-androstane-17-carboxylic acid methyl ester, as decribed in U.S. Pat. No. 4,885,280, incorporated by reference herein, (5.6 g, 16.0 mmol)), molecular sieve 4 Å (10 g) and tetramethyl urea (32 mmol, 3.8 mL) in dry CH₂Cl₂ (70 mL) under N₂ at ambient temperature is added silver triflate (4.1 g, 16 mmol). The mixture is continuously stirred for 10 min. before the compound, 2, 3, 6-trideoxy-4-benzoyl-1-chloro-β-L-mannopyranose (4.0 g, 16 mmol) is introduced in a solution of CH₂Cl₂ (370 mL). The resulting mixture is stirred in the dark for 24 h. After filtration, NaHCO₃ aqueous (saturated, 20 mL) is added to the filtrate. After stirring for 15 min. the organic phase is washed with NaHCO₃ aqueous (5%), H₂O and brine, dried with NaSO₄ and evaporated under reduced pressure to yield a residue. Purification by chromatography (silica gel, elution with CHCl₃/MeOH in gradient from 500:10 with 3 drops of NH₄OH to 500:50 with 15 drops of NH₄OH) yields the product (3β, 5β, 14β, 17β)-14-amino-3-[(2', 3', 6'-trideoxy-4-benzoyl-α-L-mannopyranosyl)-oxy]androstane-17-carboxylic acid methyl ester and starting aglycone (3β, 5β, 14β, 17β)-14-amino-3-hydroxy-androstane-17-carboxylic acid methyl ester. The glycoside is crystallized from hexane/ethyl ether (10:1) and recrystallized from ethyl acetate/hexane to yield a white crystalline solid final product.

Example 2

Synthesis of (3β, 5β, 14β, 17β)-14-Amino-3-[(2', 3', 6'-trideoxy-4-benzoyl-β-L-mannopyranosyl)-oxy]-androstane-17-carboxylic acid methyl ester

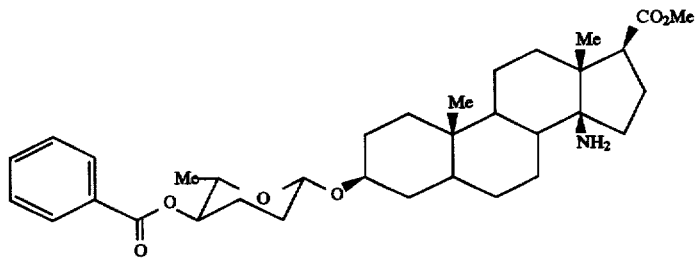

The combined mother liquid, from the Example 1 preparation of (3β, 5β, 14β, 17β)-14-amino-3-[(2', 3', 6'-trideoxy-4-benzoyl-α-L-mannopyranosyl)-oxy]-androstane-17-carboxylic acid methyl ester is concentrated. (3β, 5β, 14β, 17β)-14-amino-3-[(2', 3', 6'-trideoxy-4-benzoyl-β-L-mannopyranosyl)-oxy]-androstane-17-carboxylic acid methyl ester final product is precipitated from hexane as an amorphous solid.

Example 3

Synthesis of (3β, 5β, 14β, 17β)-14-Amino-3-[(2', 3', 6'-trideoxy-α-L-mannopyranosyl)-oxy]-androstane-17-carboxylic acid methyl ester

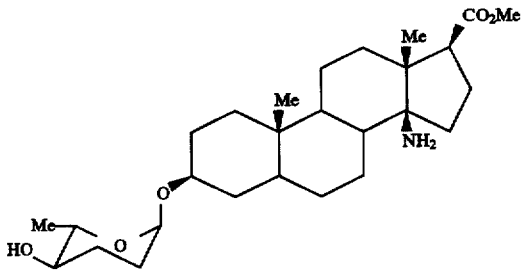

To a stirred solution of (3β, 5β, 14β, 17β)-14-amino-3-[(2', 3', 6'-trideoxy-4-benzoyl-α-L-mannopyranosyl)-oxy]-androstane-17-carboxylic acid methyl ester (318 mg, 0.56 mmol) in anhydrous MeOH (15 mL) at ambient temperature is added NaOMe (300 mg, 5.6 mmol). The mixture is stirred for 12 h under $N_2$. Removal of the solvent under vacuum yields a white solid residue. This crude mixture is then partitioned in $CHCl_3$ and $H_2O$. The aqueous layer is extracted three times with $CHCl_3$. The combined extracts are washed with $H_2O$ and brine, are dried and evaporated to yield 210 mg of solid product. Purification by chromatography (silica gel, eluded with $CH_2Cl_2$/MeOH/$NH_4$OH in gradient from 500:20:4 drops to 500:40:10 drops) yields the pure (3β, 5β, 14β, 17β)-14-amino-3-[(2', 3', 6'-trideoxy-α-L-mannopyranosyl)-oxy]-androstane-17-carboxylic acid methyl ester as a white crystalline solid final product.

carboxylic acid methyl ester, crystallized as white solid from ethyl ether and hexane.

Example 5

Synthesis of (3β, 5β, 14β, 17β)-14-Amino-3-{[6'-deoxy-2',3'-(1-methylethylidene)-4'-benzoyl-α-L-mannopyranosyl]-oxy}-androstane-17-carboxylic acid methyl ester

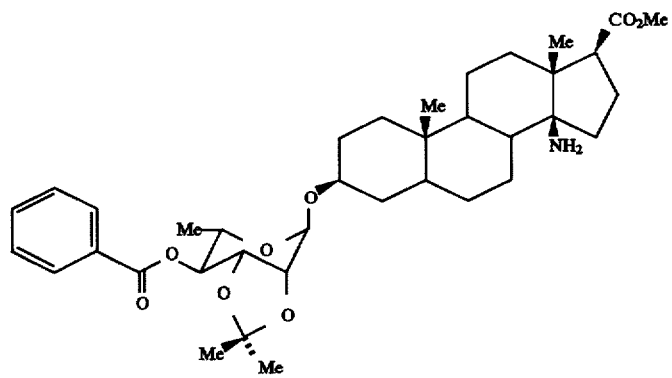

Example 4

Synthesis of (3β, 5β, 14β, 17β)-14-Amino-3-[(2', 3', 6'-trideoxy-β-L-mannopyranosyl)-oxy]-androstane-17-carboxylic acid methyl ester

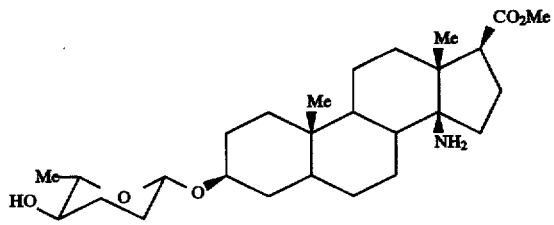

A mixture of (3β, 5β, 14β, 17β)-14-amino-3-[(2', 3', 6'-trideoxy-4-benzoyl-β-L-mannopyranosyl)-oxy]-androstane-17-carboxylic acid methyl ester (500 mg, 0.88 mmol) and NaOMe (240 mg, 4.5 mmol) in anhydrous MeOH (15 mL) is stirred at ambient temperature under $N_2$ for 24 h. Removal of the solvent yields a crude solid residue which is partitioned with $CHCl_3$ and $H_2O$. The aqueous layer is extracted to twice with $CHCl_3$. The combined extracts are washed with brine, are dried and are evaporated under vacuum to yield the product. Purification by chromatography (eluting with $CHCl_3$/MeOH/$NH_4$OH in gradient from 500:20:5 drops to 500:30:10 drops) yields the compound, (3β, 5β, 14β, 17β)-14-amino-3-[(2', 3', 6'-trideoxy-β-L-mannopyranosyl)-oxy]-androstane-17-

Preparation of (3β, 5β, 14β, 17β)-14-amino-3-{[6'-deoxy-2',3'-(1-methylethylidene)-α-L-mannopyranosyl]-oxy}-androstane-17-carboxylic acid methyl ester hydrogen chloride To a suspended solution of (3β, 5β, 14β, 17β)-14-amino-3-[(6'-deoxy-α-L-mannopyranosyl)-oxy]-androstane-17-carboxylic acid methyl ester hydrogen chloride, as described in U.S. Pat. No. 4,885,280, incorporated by reference herein, (12 g, 22.6 mmol) in 2,2-dimethoxypropane (65 mL) and dry DMF (80 mL) is added HCl etherate (catalytic amount). The mixture is stirred for 12 h at ambient temperature. Removal of the solvent under vacuum yields a light yellow residue which is crystallized from ethyl ether/hexane (11.2 g, 92%) as a white solid, (3β, 5β, 14β, 17β)-14-amino-3-[{6'-deoxy-2',3'-(1-methylethylidene)-α-L-mannopyranosyl}-oxy]-androstane-17-carboxylic acid methyl ester hydrogen chloride salt final product.

Preparation of (3β, 5β, 14β, 17β)-14-amino-3-{[6'-deoxy-2',3'-(1-methylethylidene)-4'-benzoyl-α-L-mannopyranosyl]-oxy}-androstane-17-carboxylic acid methyl ester To a stirred solution of (3β, 5β, 14β, 17β)-14-amino-3-[{6'-deoxy-2',3'-(1-methylethylidene)-α-L-mannopyranosyl}-oxy]-androstane-17-carboxylic acid methyl ester hydrogen chloride salt (8.3 g, 14.5 mmol) in anhydrous $CH_2Cl_2$ (150 mL) is added dry pyridine (2.4 mL), benzoyl chloride (3.4 mL) and DMAP (177 mg, 1.4 mmol) at 0° C. under $N_2$. The temperature is allowed to warm to room temperature in 2 h. The reaction goes to completion in 3 days. Evaporation of the solvent yields a crude product (10 g). Purification by recrystallization in ethyl acetate/MeOH yields the HCl salt of the product. The salt is dissolved in $CH_2Cl_2$ and is washed with $NaHCO_3$ aqueous (5%) and $H_2O$, and is dried and evaporated to yield the (3β, 5β, 14β, 17β)-14-amino-3-{[6'-deoxy-2',3'-(1-methylethylidene)-4'-benzoyl-α-L-mannopyranosyl]-oxy}-androstane-17-carboxylic acid methyl ester final product.

Example 6

Synthesis of (3β, 5β, 14β, 17β)-14-Amino-3-[(6'-deoxy-4'-benzoyl-α-L-manno-pyranosyl)-oxy]-androstane-17-carboxylic acid methyl ester

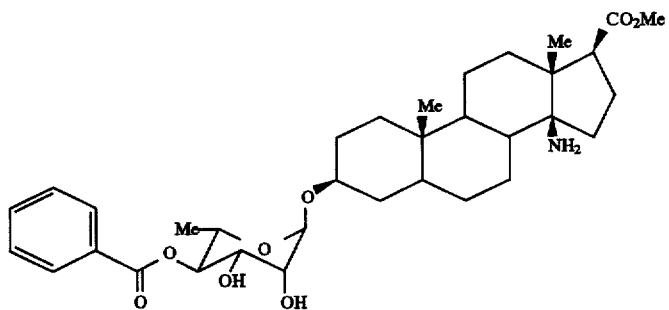

To a suspended solution of (3β, 5β, 14β, 17β)-14-amino-3-{[6'-deoxy-2',3'-(1-methylethylidene)-4'-benzoyl-α-L-mannopyranosyl]-oxy}-androstane-17-carboxylic acid methyl ester (831 mg, 1.3 mmol) in MeOH (50 mL) is added HCl etherate (saturated, 2.0 mL) at ambient temperature. The solution quickly turns clear. The reaction reaches completion after 1 h. Evaporation of the solvent yields a residue which is dissolved in $CH_2Cl_2$ (30 mL) and is mixed with $NaHCO_3$ (5%). The mixture is stirred for 15 min. The aqueous layer is extracted with $CH_2Cl_2$. The combined organic layers are dried over $Na_2SO_4$. Removal of the solvent yields a pure solid product (3β, 5β, 14β, 17β)-14-amino-3-[(6'-deoxy-4'-benzoyl-α-L-mannopyranosyl)-oxy]-androstane-17-carboxylic acid methyl ester.

Example 7

Synthesis of (3β, 5β, 14β, 17β)-14-Amino-3-[(2', 3', 6'-trideoxy-4'-O-benzoyl-α-L-erythro-hex-2-enopyranosyl)-oxy]-androstane-17-carboxylic acid methyl ester Preparation of (3β, 5β, 14β, 17β)-14-amino-3-[(6'-deoxy-4'-benzoyl-2', 3'-diphenyl thionoformyl-α-L-mannopyranosyl)-oxy]-androstane-17-carboxylic acid methyl ester To a solution of (3β, 5β, 14β, 17β)-14-amino-3-[(6'-deoxy-4'-benzoyl-α-L-mannopyranosyl)-oxy]-androstane-17-carboxylic acid methyl ester (720 mg, 1.19 mmol) and DMAP (580 mg, 4.8 mmol) in anhydrous $CH_3CN$ (15 mL) at 0° C. is added phenyl chlorothionoformate (0.41 mL, 3 mmol) dropwise under $N_2$. The mixture is allowed to warm up to ambient temperature. After 12 h, the solvent is removed under vacuum. The residue is partitioned in $CH_2Cl_2$ and $NH_4Cl$ aqueous. The separated aqueous layer is extracted with $CH_2Cl_2$. The combining organic extracts are washed with $NaHCO_3$ (5%), are dried and are evaporated to yield a crude product. Purification by chromatography (eluting with $CH_2Cl_2$/MeOH in gradient from 500:7 with 3 drops of $NH_4OH$ to 500:20 with 10 drops of $NH_4OH$) yields (3β, 5β, 14β, 17β)-14-amino-3-[(6'-deoxy-4'-benzoyl-2', 3'-diphenyl thionoformyl-α-L-mannopyranosyl)-oxy]-androstane-17-carboxylic acid methyl ester (280 mg; another 92 mg is obtained from a second purification of the mother liquid, 36%).

Preparation of (3β, 5β, 14β, 17β)-14-amino-3-[(2', 3', 6'-trideoxy-4'-O-benzoyl-α-L-erythro-hex-2-enopyranosyl)-oxy]-androstane-17-carboxylic acid methyl ester To a solution of (3β, 5β, 14β, 17β)-14-amino-3-[(6'-deoxy-4'-benzoyl-2', 3'-diphenyl thionoformyl-α-L-mannopyranosyl)-oxy]-androstane-17-carboxylic acid methyl ester (280 mg, 0.32 mmol) in toluene (30 mL) is added AIBN (11 mg, 0.07 mmol) and n-$Bu_3SnH$ (258 mg, 0.96 mmol). The solution is bubbled through with $N_2$ for 10 min. The reaction mixture is then heated to reflux for 2 h. Evaporation of the solvent yields a residue which is purified

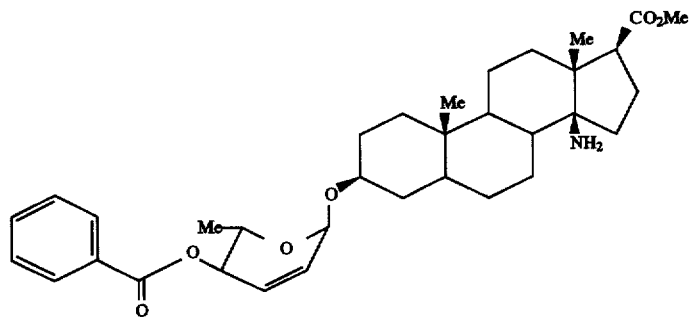

by chromatography. Eluting with $CH_2Cl_2$/MeOH in gradient from 400:7 with 2 drops of $NH_4OH$ to 400:30 with 11 drops of $NH_4OH$ furnishes (3β,5β,14β,17β)-14-amino-3-[(2',3',6'-trideoxy-4'-O-benzoyl-α-L-erythro-hex-2-enopyranosyl)-oxy]-androstane-17-carboxylic acid methyl ester as a crystalline solid.

Example 8

Synthesis of (3β, 5β, 14β, 17β)-14-Amino-3-{[6'-deoxy-2',3'-(1-methylethylidene)-4'-O-t-butyldimethylsilyl-α-L-mannopyranosyl]-oxy}-androstane-17-carboxylic acid methyl ester

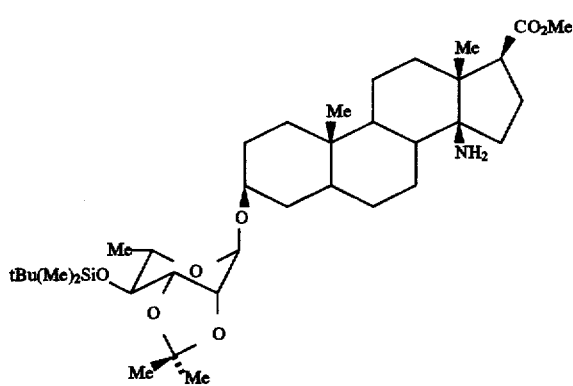

To a solution of (3β, 5β, 14β, 17β)-14-amino-3-{[6'-deoxy-2',3'-(1-methylethylidene)-α-L-mannopyranosyl]-oxy}-androstane-17-carboxylic acid methyl ester (6.61 g, 12.3 mmol) and imidazole (1.7 g, 24.6 mmol) in anhydrous DMF (50 mL) under $N_2$ is added TBDMSiCl (2.2 g, 14.8 mmol) in DMF (10 mL). The mixture is stirred at ambient temperature for 4 h. If TLC ($CH_2Cl_2$/MeOH 10:1.5) indicates that the reaction is incomplete, more TBDMSiCl (0.7 g, 4.6 mmol) is added. After 14 h ice water is poured into the reaction mixture and the solution is extracted four times with $CH_2Cl_2$ (total 200 mL). The extract is washed with $H_2O$, $NaHCO_3$ aqueous (2%) and brine, and is dried over $Na_2SO_4$. After concentration, this light yellow residue is crystallized from MeOH. Filtration yields (3β, 5β, 14β, 17β)-14-amino-3-{[6'-deoxy-2', 3'-(1-methylethylidene)-4'-O-t-butyldimethylsilyl-α-L-mannopyranosyl]-oxy}-androstane-17-carboxylic acid methyl ester as white crystalline solid.

Example 9

Synthesis of (3β, 5β, 14β, 17β)-14-Amino-3-[(3',6'-dideoxy-2',4'-O-dibenzoyl-α-L-mannopyranosyl)-oxy]-androstane-17-carboxylic acid methyl ester

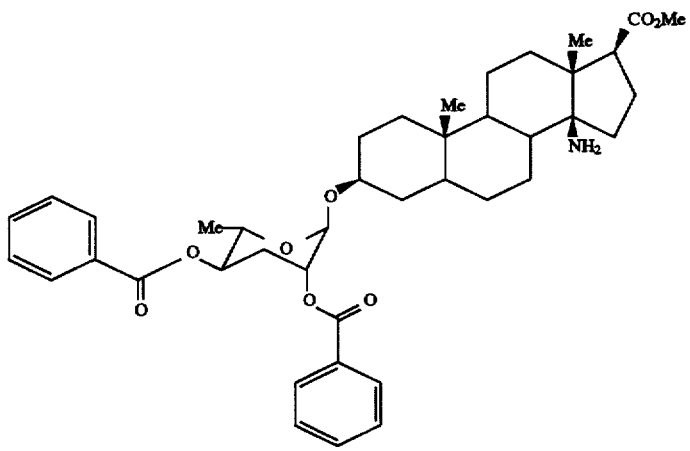

Preparation of methyl 6-deoxy-α-L-mannopyranoside, 2,4-O-dibenzoate

See, Yang, G-B.; Kong, F. *Carbohydr. Res.* 1991, 211, 179. Kovac, P.; Edgar, J. *J. Org. Chem.* 1992, 57, 2455, incorporated by reference herein.

Preparation of methyl 6-deoxy-3-O-phenylthiono-formyl-α-L-mannopyranoside, 2,4-O-dibenzoate To a solution of 6-deoxy-α-L-mannopyranoside, 2,4-O-dibenzoate (100 mg, 0.26 mmol) and DMAP (95 mg, 0.78 mmol) in anhydrous $CH_3CN$ (6 mL) at 0° C. under $N_2$ is added phenyl chlorothionoformate (54 mL, 0.39 mmol). The solution is stirred at 0° C. for 1 h and then at ambient temperature for 6 h. Precipitation occurs during the reaction period. The mixture is diluted with $CH_2Cl_2$ (15 mL) and is washed with HCl (aq) (0.5N), $H_2O$, $Na_2CO_3$ (aq) (5%) and brine, and is dried. Evaporation of the solvent furnishes methyl 6-deoxy-3-O-phenylthiono-formyl-α-L-mannopyranoside, 2,4-O-dibenzoate which is used for the next reaction without further purification. Further purification by chromatography (eluting with hexane/ethyl acetate 10:1) yields a white solid.

Preparation of methyl 3,6-dideoxy-α-L-mannopyranoside, 2,4-O-dibenzoate

To a solution of methyl 6-deoxy-3-O-phenylthionoformyl-α-L-mannopyranoside, 2,4-O-dibenzoate (3.5 g, 6.7 mmol) in toluene (120 mL) is added AIBN (55 mg, 0.34 mmol) and n-$Bu_3SnH$ (2.6 mL, 13.4 mmol). The solution is deoxygenated by passing through $N_2$ gas for 20 min. The reaction flask is placed in an oil bath (120° C.). After 1.5 h TLC indicates that the reaction is complete. Evaporation of the solvent yields a residue. Purification by chromatography (eluting with hexane/ethyl acetate in gradient from 500:20 to 500:50) yields methyl 3,6-dideoxy-α-L-mannopyranoside, 2,4-O-dibenzoate (1.8 g, 70% in two steps from 6-deoxy-α-L-mannopyranoside, 2,4-O-dibenzoate).

Preparation of (2S,3R,5S,6R)-2-chloro-3,5-O-dibenzoyl-6-methyl pyrane

To a magnetically stirred solution of methyl 3,6-dideoxy-α-L-mannopyranoside, 2,4-O-dibenzoate (1.2 g, 3.3 mmol) in dry $CH_2Cl_2$ (60 mL) at −78° C. under nitrogen was added $BCl_3$ dropwise (1.0M in $CH_2Cl_2$, 6.5 mL). After complete consumption of the starting material (30 min), $NaHCO_3$ aqueous (2%, 30 mL) is poured into the mixture at low temperature (the aqueous layer is initially frozen). The separated organic layer is dried with $Na_2SO_4$, is filtered, is then further dried with molecular sieve 4 Å. This solution is directly used for the next step of the reaction. A small portion of the solution is evaporated under reduced pressure to provide a colorless liquid product, (2S,3R,5S,6R)-2-chloro-3,5-O-dibenzoyl-6-methyl pyrane.

Preparation of (3β, 5β, 14β, 17β)-14-amino-3-[(3',6'-dideoxy-2',4'-O-dibenzoyl-α-L-mannopyranosyl)-oxy]-androstane-17-carboxylic acid methyl ester To a magnetically stirred suspended solution of aglycone (3β, 5β, 14β, 17β)-14-amino-3-hydroxy-androstane-17-carboxylic acid methyl ester, as described in U.S. Pat. No. 4,885,280, incorporated by reference herein, (1.7 g, 5.0 mmol), molecular sieve 4 Å (3 g) and tetramethyl urea (6.6 mmol, 0.78 mL) in dry $CH_2Cl_2$ (20 mL) under $N_2$ at ambient temperature is added silver triflate (1.0 g, 4.0 mmol). The mixture is continuously stirred for 10 min before a solution of (2S,3R,5S,6R)-2-chloro-3,5-O-dibenzoyl-6-methyl pyrane (1.2 g, 3.3 mmol) in $CH_2Cl_2$ (180 mL) is introduced. The resulting mixture is stirred in the dark for 19 h. After filtration $NaHCO_3$ aqueous (saturated, 20 mL) is added to the filtrate. After 15 min. stirring the organic phase is washed with $NaHCO_3$ aqueous (2%), $H_2O$ and brine, is dried with $Na_2SO_4$ and is evaporated under vacuum to provide a residue. This crude mixture is dissolved in $CH_2Cl_2$. Most of the remaining (3β, 5β, 14β, 17β)-14-amino-3-hydroxy-androstane-17-carboxylic acid methyl ester is crystallized out of the solution. The product is further purified by chromatography (silica gel, elution with $CH_2Cl_2$/MeOH in gradient from 500:10 with 3 drops of $NH_4OH$ to 500:20with 8 drops of $NH_4OH$) to yield (3β, 5β, 14β, 17β)-14-amino-3-[(3',6'-dideoxy-2',4'-O-dibenzoyl-α-L-mannopyranosyl)-oxy]-androstane-17-carboxylic acid methyl ester, which is recrystallized from hexane/ethyl ether (10:1) as a white solid.

Example 10

Synthesis of (3β, 5β, 14β, 17β)-14-Amino-3-[(3',6'-dideoxy-α-L-mannopyranosyl)-oxy]-androstane-17-carboxylic acid methyl ester

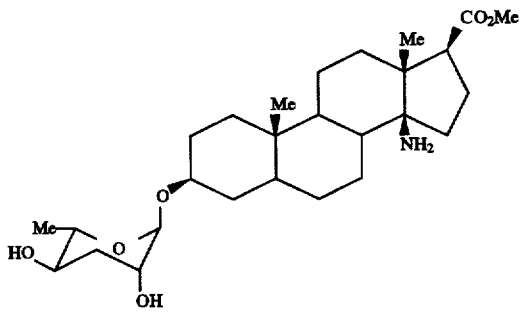

To a stirred solution of (3β, 5β, 14β, 17β)-14-Amino-3-[(3',6'-dideoxy-2',4'-O-dibenzoyl-α-L-mannopyranosyl)-oxy]-androstane-17-carboxylic acid methyl ester (6.2 g, 9.2 mmol) in anhydrous MeOH (40 mL) at ambient temperature is added NaOMe (4.0 g, 73.6 mmol). The mixture is stirred for 24 h under $N_2$. Removal of the solvent under reduced pressure yields a white solid residue. This crude mixture is partitioned in $CHCl_3$ and $H_2O$. The aqueous layer is extracted with $CHCl_3$ three times. The combined extracts are washed with brine, are dried and are evaporated to yield a crude product. Purification by chromatography (silica gel, eluded with $CH_2Cl_2$/MeOH/$NH_4OH$ in gradient from 500:10:3 drops to 500:40:12 drops) provides a pure (3β, 5β, 14β, 17β)-14-amino-3-[(3',6'-dideoxy-α-L-mannopyranosyl)-oxy]-androstane-17-carboxylic acid methyl ester as white crystal.

Example 11

Synthesis of (3β, 5β, 14β, 17β)-14-Amino-3-[(3',6'-dideoxy-2'-O-benzoyl-α-L-mannopyranosyl)-oxy]-androstane-17-carboxylic acid methyl ester

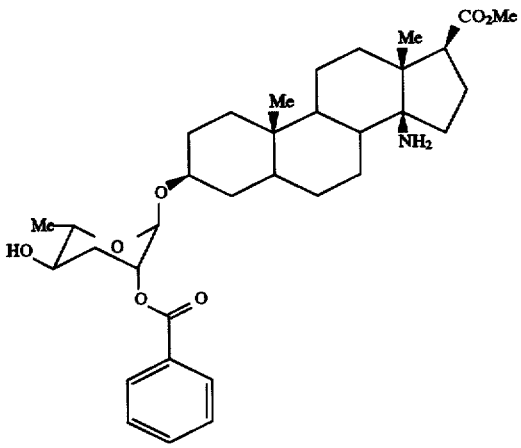

Chromatographic separation of the crude mixture obtained in Example 10, 3β, 5β, 14β, 17β)-14-amino-3-[(3', 6'-dideoxy-α-L-mannopyranosyl)-oxy]-androstane-17-carboxylic acid methyl ester, also yields a less polar product, (3β, 5β, 14β, 17β)-14-amino-3-[(3',6'-dideoxy-2'-O-benzoyl-α-L-mannopyranosyl)-oxy]-androstane-17-carboxylic acid methyl ester.

Example 12

Synthesis (3β, 5β, 14β, 17β)-14-Amino-3-[(3',6'-dideoxy-2',4'-O-diacetyl-α-L-mannopyranosyl)-oxy]-androstane-17-carboxylic acid methyl ester, hydrogen chloride

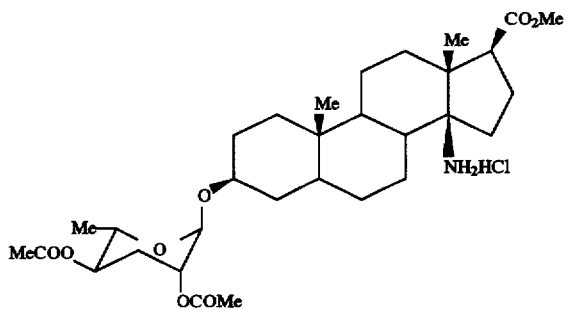

(3β, 5β, 14β, 17β)-14-amino-3-[(3',6'-dideoxy-α-L-mannopyranosyl)-oxy]-androstane-17-carboxylic acid methyl ester (840 mg, 1.75 mmol) is suspended in MeOH (10 mL) at −5° C. Methanolic HCl is added dropwise and the solid goes into solution. The stirring is continued for 10 min. The solution is evaporated at 0° C. to provide a white solid (3β, 5β, 14β, 17β)-14-amino-3-[(3',6'-dideoxy-α-L-mannopyranosyl)-oxy]-androstane-17-carboxylic acid methyl ester hydrogen chloride salt (quantitative yield). This salt is subsequently dissolved in a mixed solvent, acetic anhydride/CH₂Cl₂ (1:1) (30 mL) and four drops of dry pyridine are added. The mixture is stirred at ambient temperature under N₂ for 48 h. After concentration the residue is precipitated from hexane/Et₂O to yield (3β, 5β, 14β, 17β)-14-amino-3-[(3',6'-dideoxy-2',4'-O-diacetyl-α-L-mannopyranosyl)-oxy]-androstane-17-carboxylic acid methyl ester hydrogen chloride as a white crystal.

Example 13

Synthesis of (3β, 5β, 14β, 17β)-14-Amino-3-[(6'-deoxy-α-L-mannopyranosyl)-oxy]-androstane-17-methyl amide, hydrogen chloride

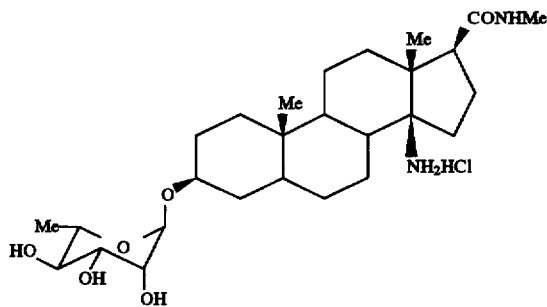

A solution of (3β, 5β, 14β, 17β)-14-amino-3-[(6'-deoxy-α-L-mannopyranosyl)-oxy]-androstane-17-carboxylic acid methyl ester hydrogen chloride, as described in U.S. Pat. No. 4,885,280, incorporated by reference herein, (500 mg, 0.94 mmol) in MeOH (10 mL) is added to a steel bomb and cooled to −5° C. Methylamine is bubbled into the solution until the volume increases by 1 mL. The bomb is sealed and is placed into a 125° C. oven for 3 days. After the bomb is cooled to −10° C. the seal is opened and the solution is transferred into a flask and is evaporated under vacuum to yield a solid. Recrystallization of this crude product in MeOH/ethyl acetate furnishes (3β, 5β, 14β, 17β)-14-amino-3-[(6'-deoxy-α-L-mannopyranosyl)-oxy]-androstane-17-methyl amide hydrogen chloride (quantitative yield) as a crystalline solid.

Example 14

Synthesis of (3β, 5β, 14β, 17β)-14-Amino-3-[(6'-deoxy-2',3',4'-O-triacetyl-α-L-mannopyranosyl)-oxy]-androstane-17-methyl amide, hydrogen chloride

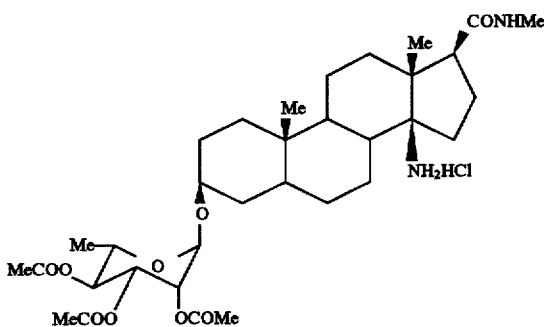

A solution of (3β, 5β, 14β, 17β)-14-amino-3-[(6'-deoxy-α-L-mannopyranosyl)-oxy]-androstane-17-methyl amide hydrogen chloride (1.25 g, 2.35 mmol), dry pyridine (0.5 mL) and acetic anhydride (20 mL) is stirred at ambient temperature under N₂ for 3 days. Evaporation of the solvent under vacuum yields a semi-solid residue. Solid precipitates are formed upon the addition of ethyl acetate. The solid obtained from filtration is recrystallized in ethyl acetate and MeOH (10:0.5) to provide (3β,5β,14β,17β)-14-amino-3-[(6'-deoxy-2',3',4'-O-triacetyl-α-L-mannopyranosyl)-oxy]-androstane-17-methyl amide hydrogen chloride as a white crystalline solid.

Example 15

14β-amino-3β-[(tri-2',3',4'-O-methyl)-α-(L)-rhamnopyranosyloxy]-5β-androstane-17β-carboxylic acid, methyl ester

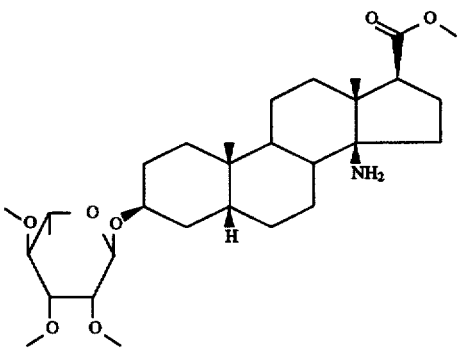

1.0 g of 14β-azido-3β-[α-(L)-rhamnopyranosyloxy]-5β-androstane-17β-carboxylic acid, methyl ester, obtained as described in U.S. Pat. No. 4,885,280, incorporated by reference herein, is dissolved under argon atmosphere, in 20 ml of dimethylformamide under stirring in an ice bath. 250 mg of a suspension of sodium hydride (60% in oil) and 1 ml of methyl iodide are added to the solution, and the reaction is continued under stirring at 0° C. 5 hours.

The reaction mixture is neutralized with acetic acid, washed with 80 ml sodium bicarbonate, and extracted with ethyl acetate, and then washed with water and a saturated solution of NaCl. After purification by chromatography on silica gel column and eluting with a chloroform-ethyl alcohol mixture (99:1), the 14β-azido-3β-[(tri-2',3',4'-O-methyl)-α-(L)-rhamnopyranosyloxy]-5β-androstane-17β-carboxylic acid, methyl ester is obtained.

The azido group is converted into an amino group after addition of the above azido derivative (640 mg) into a methyl alcohol solution (60 ml) of hydrazine hydrate, and addition of Pd(OH)$_3$ as catalyst (320 mg). The reaction mixture is heated under reflux for 1 hour.

After filtration on Celite, extraction with ethyl acetate, washing with water and with a saturated NaCl solution, the residue is purified by flash chromatography, eluted with a heptane-ethyl acetate-triethylamine (49:49:2) mixture to yield 14β-amino-3β-[(tri-2',3',4'-O-methyl)-α-(L)-rhamnopyranosyloxy]-5β-androstane-17β-carboxylic acid, methyl ester.

Example 16

14β-amino-3b[(3'-O-methyl)-α(L)-rhamnopyranosyloxy]-5β-androstane-17β-carboxylic acid, methyl ester

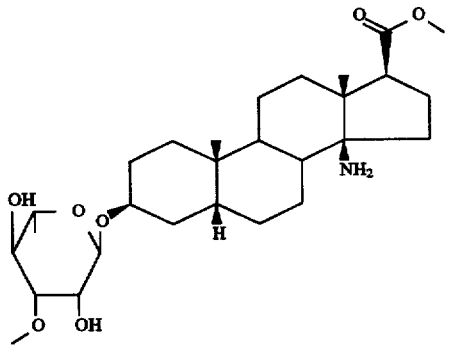

This compound is prepared as described in Example 15 but using 360 mg of 14β-azido-3β-[(3'-O-methyl)-α-(L)-rhamnopyranosyloxy]-5β-androstane-17β-carboxylic acid, methyl ester, instead of 14β-azido-3β-[(tri-2',3',4'-O-methyl)-α-(L)-rhamnopyranosyloxy]-5β-androstane-17β-carboxylic acid, methyl ester.

14β-amino-3β-[(3'-O-methyl)-α-(L)-rhamnopyranosyloxy]-5β-androstane-17β-carboxylic acid, methyl ester is obtained.

Example 17

14β-amino-3β-[(2',4'-di-O-acetyl-3'-O-methyl)-α-(L)-rhamnopyranosyloxy]-5β-androstane-17β-carboxylic acid, methyl ester

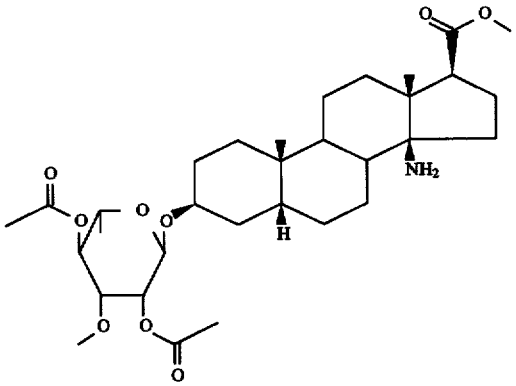

The 14β-azido-3β-[(3'-O-methyl)-α-(L)-rhamnopyranosyloxy]-5β-androstane-17β-carboxylic acid, methyl ester (370 mg) used in Example 16 is dissolved in 5 ml methylene chloride, and to this solution, 0.2 ml of pyridine, 0.2 ml of acetic anhydride, and then 2.5 mg of dimethyl amino pyridine are added. The mixture is stirred for 4 hours at room temperature, and a part of the solvent is removed by heating. 10 ml of ammonia are poured into the solution, and the residue is extracted with ethyl acetate, and then washed with water and a saturated NaCl solution.

After HPLC chromatography, 14β-azido-[(2',4'-di-O-acetyl-3'-O-methyl)-α-(L)-rhamnopyranosyloxy]-5β-androstane-17β-carboxylic acid, methyl ester is obtained. The 14β-amino-3β-[(2',4'-di-O-acetyl-3'-O-methyl)-α-(L)-rhamnopyranosyloxy]-5bn-androstane-17β-carboxylic acid, methyl ester is obtained from the above 14-azido derivative by the same process as in Example 16.

Example 18

14β-amino-3β-[(tri-2',3',4'-O-benzoyl)-α-(L)-rhamnopyranosyloxy]-5-androstane-17β-carboxylic acid, methyl ester

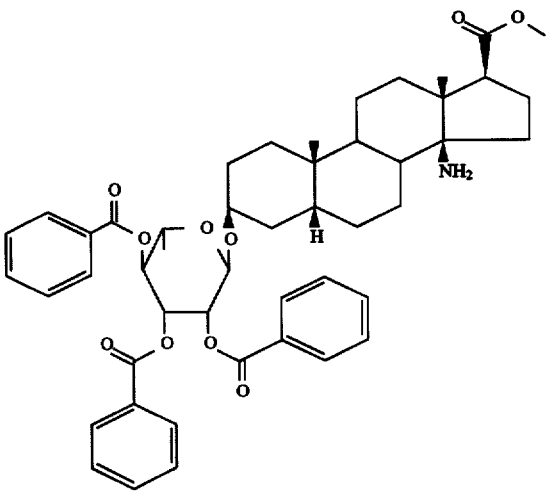

13 g of 14β-azido-3β-hydroxy-5β-androstane-17β-carboxylic acid, methyl ester, and 8.3 ml of tetramethylurea are placed in 3-neck flask equipped with a magnetic stirrer, containing about 200 ml of methylene chloride. The mixture is stirred under nitrogen atmosphere, a molecular sieve (15 g, 4 Å) is added, and the mixture is left under stirring for 1 hour. 12.6 g of zinc trifluoro methane sulfonate are added, and then 28 g of tri-O-benzoyl-rhamnosyl bromide dissolved in 300 ml of methylene chloride, dropwise. The reaction is continued overnight under stirring at room temperature.

After addition of a saturated solution of sodium bicarbonate, filtration, washing with methylene chloride, washing with water, and then with a saturated NaCl solution, extracting with methylene chloride and drying, crystallisation in methyl alcohol, the 14β-azido-3β-[(tri-2',3',4'-O-benzoyl)-α-(L)-rhamnopyranosyloxy]-5β-androstane-17*-carboxylic acid, methyl ester, is obtained.

The above 14-azido derivative is refluxed with tellurium and sodium borohydride for two hours under argon. The reaction mixture is allowed to cool until room temperature, and 270 mg of the above 14-azido ester in solution in 2 ml of absolute deoxygenated ethyl alcohol are added.

The mixture is kept under stirring for 21 hours, and then for 15 minutes at open air so that the reagent in excess is removed. After filtration on Celite, eluting with a chloroform-ethyl alcohol mixture (90:10), the filtrate is evaporated until dry. The bases are diluted with toluene and extracted with a 2% aqueous sulfamic acid solution. After addition of sodium carbonate and extraction with methylene chloride, 189 mg of base and 42 mg of neutral compound are obtained.

Sodium chloride is added until saturation and the polar compound is obtained, which is also present in the first basic extract. The compound is purified on a silica gel column to obtain the 14β-amino-3β-[(tri-2',3',4'-O-benzoyl)-α-(L)-rhamnopyranosyloxy]-5β-androstane-17α-carboxylic acid, methyl ester.

Example 19

14β-amino-3β-[(2'-O-methyl)-α-(L)-rhamnopyranosyloxy]-5β-androstane-17β-carboxylic acid, methyl ester

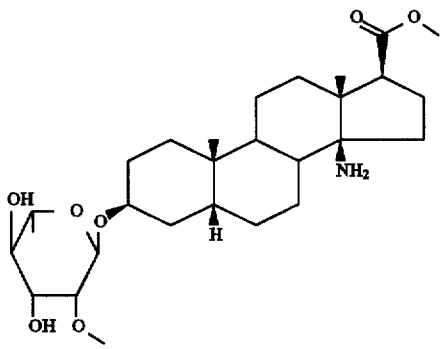

200 mg of 14β-azido-3β-[(3'-O-benzoyl-2'-O-methyl)-α-(L)-rhamnopyranosyloxy]-5β-androstane-17β-carboxylic acid, methyl ester and 0.2 ml of sodium methanolate are caused to react overnight in a mixture solution of 10 ml of methyl alcohol and 10 ml of methylene chloride, under argon, while stirring at room temperature.

After extraction with methylene chloride, with water and with a saturated NaCl solution, the residue is purified by chromatography, eluting with a methylene chloride-acetone (85:15) mixture, followed by a crystallisation in a methyl alcohol-isopropyl ether mixture.

115 mg of the 14β-azido-3β-[(2'-O-methyl-α-(L)-rhamnopyranosyloxy]-5β-androstane-17β-carboxylic acid, methyl ester obtained as indicated above are treated with hydrazine hydrate in the presence of a catalyst according to the method of Example 15, and 14β-amino-3β-[(2'-O-methyl)-α-(L)-rhamnopyranosyloxy]-5β-androstane-17β-carboxylic acid, methyl ester is obtained.

Example 20

14β-amino-3β-[(tetra-O-acetyl)-β(D)-glucopyranosyloxy]-5β-androstane-17β-carboxylic acid, methyl ester

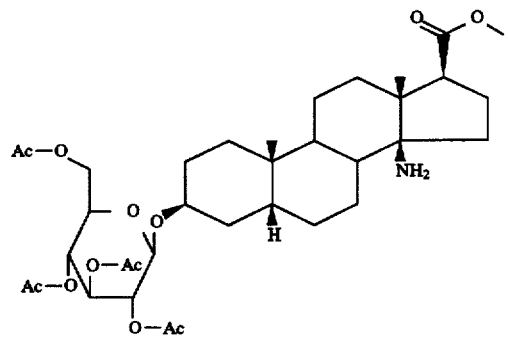

1.5 g of 14β-amino-3β-hydroxy-5β-androstane-17β-carboxylic acid, methyl ester, 0.65 g of tetramethylurea 1.5 g of molecular sieve (4 Å) are dissolved in 25 ml of methylene chloride, under argon, on an ice bath. The mixture is stirred and 1.63 g of zinc trifluoro methyl sulfonate are introduced, and 5 g of tetra-O-benzoyl-α-(D)-glucosyl bromide dissolved in 22 ml of methylene chloride are slowly added in 1 hour. Then 0.6 g of zinc trifluoromethyl sulfonate are added and the temperature is increased to room temperature, and after 2 hours 0.2 g of silver trifluoromethyl sulfonate are added. The reaction is continued overnight and 0.5 g of silver trifluoromethyl sulfonate are added two times at 2 hours interval.

When the reaction is completed, 30 ml of a saturated sodium hydrogencarbonate solution are added to the reaction mixture, and the insoluble is filtered off, rinsing with methylene chloride. The filtrate is washed with sodium hydrogencarbonate, water, and then with a saturated NaCl solution. An extraction with methylene chloride is carried out, and the residue is filtered on silica (Merck 60), eluting with a methylene chloride-methyl alcohol mixture (99:1), and then with a methylene chloride-methyl alcohol-ammoniac mixture (95:5:0.5). 3 g of a oily product are obtained. The above product is treated with sodium methanolate to produce the corresponding 3-glucopyranosyloxy derivative which is acetylated with dimethyl aminopyridine and acetic anhydride in methylene chloride at room temperature for about 0.5 hour, and reduced on the 2' position by Pd/C. 14β-amino-3β-[(tetra-O-acetyl)-β-(D)-glucopyranosyloxy]-5β-androstane-17β-carboxylic acid, methyl ester, is obtained.

Example 21

14β-amino-3β-[(tri-2',3',4'-O-acetyl)-α-(L)-rhamnopyranosyloxy]-5β-androstane-17β-carboxylic acid, amide

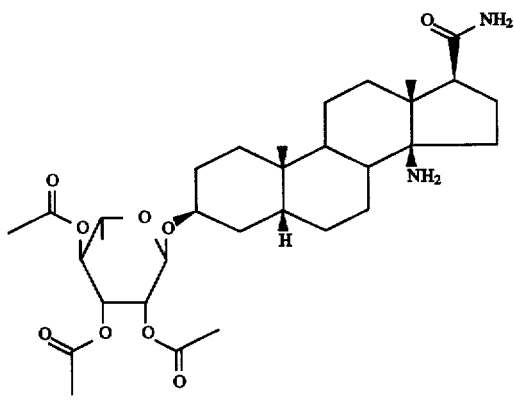

A solution of 2M trimethylaluminium (7.7 ml) in 25 ml of toluene is slowly added into a suspension of 0.8 g of ammonium chloride in 20 ml of chloroform at −10° C. The reaction mixture is cooled to room temperature with stirring for 2 hours, and a solution containing 0.8 g of 14β-azido-3β-[α-(L)-rhamnopyranosyloxy]-5β-androstane-17β-carboxylic acid methyl ester, is prepared as described in U.S. Pat. No. 4,885,280, incorporated by reference herein.

This reaction mixture is dissolved in a mixture of 25 ml of toluene and 5 ml of chloroform, is added thereto. The reaction mixture is heated under reflux for 6 hours, then at 40° C. for 16 hours. The mixture is poured into 20 ml of 2.5N hydrochloric acid in an ice bath, neutralized with ammonia.

After evaporation, the residue is filtered and purified by chromatography, eluting with a methylene chloride-methyl alcohol-ammonium hydroxide mixture (90:10:1). After filtration, 0.54 g of 14β-azido-3β-α-(L)-rhamnopyranosyloxy]-5β-androstane-17β-carboxylic acid, amide is collected (yield: 70%).

0.5 g of the above 14-azido amide is dissolved in 30 ml of chloroform, and 0.5 ml of acetic anhydride and 55 mg of dimethylaminopyridine are added thereto. The reaction mixture is stirred for 15 hours at room temperature. After extraction with methylene chloride, the organic phases are washed with water (the pH is adjusted to about 3 by adding hydrochloric acid), then with a saturated aqueous NaCl solution, and dried over sodium sulfate. The corresponding tri-O-acetyl derivative is thus obtained (yield: 100%).

The above derivative (0.5 g) is dissolved in 80 ml of methanol under argon, and 0.5 g of ammonium formate are added, followed by 0.25 g of Pd/C (10%). The reaction mixture is heated under reflux for 30 minutes, and filtered on Celite.

After evaporation until dry, 0.5 g of crude product is collected, which is purified by chromatography on a silica column, eluting with a methylene chloride-methyl alcohol-ammonium hydroxide mixture (85:15:1.5) to yield 14β-amino-3β-[(tri-2',3',4'-O-acetyl)-α-(L)-rhamnopyranosyloxy]-5β-androstane-17β-carboxylic acid, amide Final Product.

Example 22

14β-amino-20β-methoxy-3β-[(2',3'-deoxy-4'-O-acetyl)-α-(L)-rhamnopyranosyloxy]-5β,17α(H)-pregnane

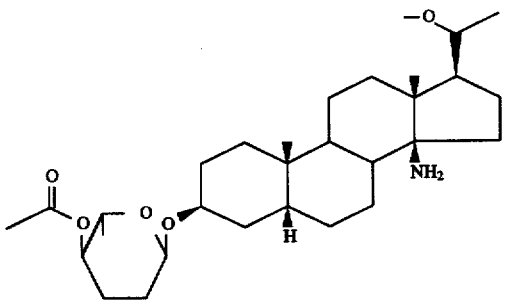

223 mg of di-3,4-O-acetyl-(L)-rhamnal are dissolved in 1 ml of dry chloroform, and a solution containing 780 mg of 14β-azido-20β-methoxy-3β-hydroxy-5β,17α (H)-pregnane and 0.09 ml of BF₃/OEt₂ in 2.8 ml of methylene chloride is added thereto.

The reaction is carried out at room temperature for 25 minutes, and then the reaction mixture is poured onto crushed ice. After extraction with methylene chloride, washing with sodium bicarbonate, the residue is purified by chromatography on silica column under pressure, eluting with a ethyl acetate hexane mixture (1:12) and 321 mg of 14β-azide-20β-methoxy-3β-[(2',3'-dehydro-2',3'-deoxy-4'-O-acetyl)-α-(L)-rhamnopyranosyloxy]-5β,17α(H)-pregnane are obtained.

The above 14-azido derivative is dissolved in 40 ml of absolute ethanol and an hydrogenation reaction is carried out in the presence of 100 mg of PtO₂ as a catalyst for 24 hours.

After evaporation to dryness, filtration and chromatography on silica column, the 14β-amino-20β-methoxy-3β-[(2',3'-deoxy-4'-O-acetyl)-α-(L)-rhamnopyranosyloxy]-5β,17α (H)-pregnane final product is obtained, which is crystallized in hexane.

Example 23

14β-amino-3β-[(di-2'-3'-O-benzoyl)-α-(L)-rhamnopyranosyloxy]-5β-androstane-17-carboxylic acid, methyl ester

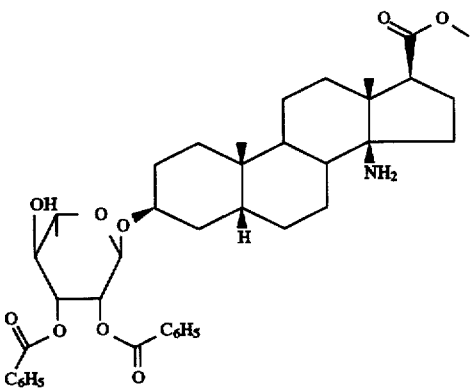

1.5 g of 14β-amino-3β-hydroxy-5β-androstane-17-carboxylic acid, methyl ester, as described in U.S. Pat. No. 4,885,280, incorporated by reference herein, 0.65 ml of tetramethylurea, and 1.1 g of molecular sieves (4 Å) are dissolved in 20 ml of methylene chloride. The mixture is stirred and 1.05 g of zinc trifluoro methyl sulfonate are introduced in 30 minutes. Then, 2.4 g of di-2,3-O-benzoyl-α-(L)-rhamnosyl bromide dissolved in 15 ml of methylene chloride are slowly added to the reaction mixture over 4 hours.

After extraction with methylene chloride, washing with water (in the presence of ammonia) and drying over sodium sulfate and evaporation until dry, 3.2 g of a yellow oily residue are obtained.

The oily residue is chromatographed on a silica column, eluting with a methylene chloride-methyl alcohol-ammonium hydroxide mixture (98:2:0.2) to yield a white powder of 14β-amino-3β-[(di-2'-3'-O-benzoyl)-α-(L)-rhamnopyranosyloxy]-5β-androstane-17-carboxylic acid, methyl ester, final product.

Example 24

Synthesis of (3β, 5β, 14β, 17β)-14-Amino-3-[(3', 6'-dideoxy-2', 4'-O-dibenzoyl-α-L-mannopyranosyl)-oxy]-androstane-17-carboxylic acid methyl ester

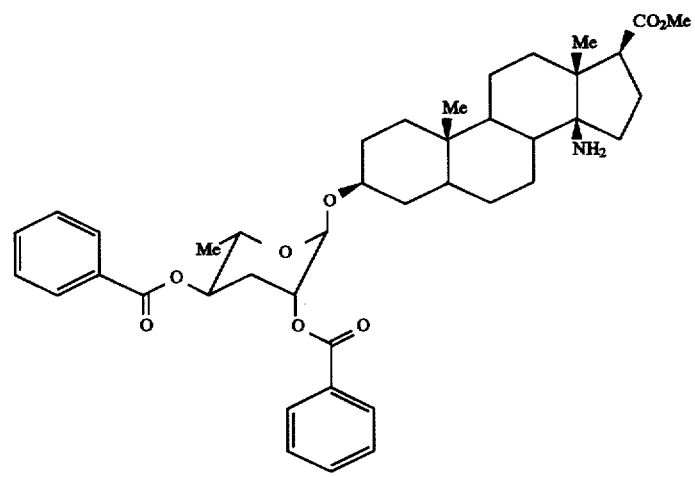

(3β, 5β, 14β, 17β)-14-Amino-3-[(3', 6'-dideoxy-2', 4'-O-dibenzoyl-α-L-mannopyranosyl)-oxy]-androstane-17-carboxylic acid methyl ester [prepared as described in Example 9 herein] can also be synthesized according to the procedures described below:

Preparation of 3,6-Dideoxy-L-erythro-hex-2-enonic acid, δ-lactone, 2,4-O-dibenzoate

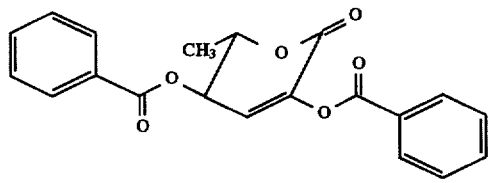

Anhydrous 6-deoxy-α-L-mannopyranosylbromide, 2,3,4-tri-O-benzoate (727.2 g, 1.35 mol) [prepared as described by Ness, R. K.; Fletcher, H. G., Hudson, C. S., *J. Am. Chem. Society*, 1951, Vol. 73, p. 296, and by Allard, P.; Dinh, T. H.; Gouyette, C.; Igolen, J.; *J. Med. Chem*, 1981, Vol. 24, p. 1291) is added to a heated (70° C.) slurry of DMSO (3.6 L) and Et₃N (451 mL, 3.24 mol) with vigorous stirring. The reaction mixture is stirred at this temperature until completion (15–20 min.) as indicated by Thin-Layer Chromatography. The reaction mixture is then poured over ice water (4.3 L). The product is extracted with EtOAc (4.3 L) and the combined extracts are washed with water (2×4.3 L) and then with aqueous saturated NaCl solution (3 L). The organic layer is dried over MgSO₄, treated with activated charcoal, filtered through Celite, and evaporated to give a yellow solid. The yellow solid is crystallized from isopropanol (150 mL) to give a white crystalline product. The mother liquor is optionally concentrated to give a second crop of product. Preparation of 3,6-Dideoxy-L-arabino-hexonic acid, δ-lactone, 2,4-O-dibenzoate

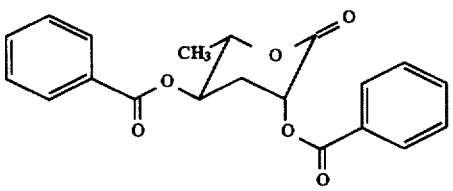

3,6-Dideoxy-L-erythro-hex-2-enonic acid, δ-lactone, 2,4-O-dibenzoate is used to make 3,6-Dideoxy-L-arabino-hexonic acid, δ-lactone, 2,4-O-dibenzoate. The procedure used is that described by Varela, O. J.; Cirelli, A. F.; De Lederkremer, R. M.; *Carbohydrate Research*, 1979, Vol. 70, p. 27, with the exception that acetone is used as a solvent instead of EtOAc.

To a solution of 3,6-dideoxy-L-erythro-hex-2-enonic acid, δ-lactone, 2,4-O-dibenzoate (168.8 g, 0.48 mol) in acetone (1.0 L) is added 10% Pd/C (1.7 g). This mixture is then shaken under an atmosphere of hydrogen (40 psi, PARR apparatus) at ambient temperature for 16 hours. The reaction mixture is then filtered through Celite and the filtrate is concentrated under reduced pressure to give a white crystalline solid.

Preparaion of 3,6-Dideoxy-α,β-L-arabino-hexopyranose 2,4-di-O-benzoate

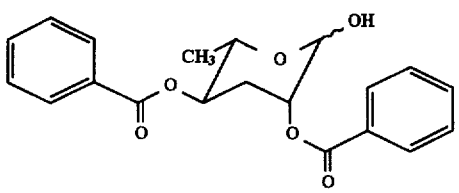

To a cooled (−10° C. to −5° C.) solution of 3,6-dideoxy-L-arabino-hexonic acid, δ-lactone, 2,4-O-dibenzoate (168 g, 0.47 mol) in THF (1.8 L) is slowly (1 hr) added a solution of Li(t-BuO)₃AlH (120.7 g, 0.47 mol) in THF (672 mL) while maintaining the temperature below 0° C. The reaction is complete after stirring for an additional 1–2 hour(s), and is monitored by Thin-Layer Chromatography. The reaction mixture is quenched with saturated aqueous NaHCO₃ solution (800 mL) to which Celite (170 g) is added. After filtering over a bed of Celite and rinsing with additional THF, the organic layer is separated, washed with saturated aqueous NaHCO₃ solution (2×1 L), dried over MgSO₄, and concentrated under reduced pressure to yield the product. The product is further purified upon dissolution in 25% EtOAc/heptane and slurrying the silica gel. The silica gel is then filtered, rinsed with 25% EtOAc/heptane, and the filtrate is concentrated to give the product as clear oil or foam.

Preparation of 3,6-Dideoxy-α-L-arabino-hexopyranose, 2,4-di-O-benzoate-1-(2,2,2-trichloroethanimidate)

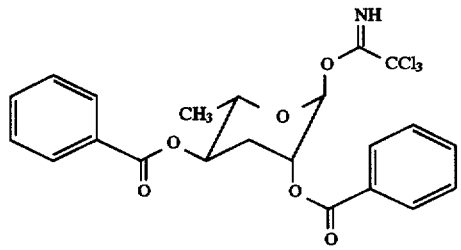

3,6-Dideoxy-α-L-arabino-hexopyranose, 2,4-di-O-benzoate-1-(2,2,2-trichloroethanimidate) is prepared according to the general procedure as described by Urban, F. J.; Moore, B. S., Breitenbach, R.; *Tetrahedron Letters*, 1990, Vol. 31, p. 4421.

To a solution of 3,6-dideoxy-α,β-L-arabino-hexopyranose 2,4-di-O-benzoate (138.0 g., 0.39 mol) in CH₂Cl₂ (1.0 L) is added Cs₂CO₃ (5.6 g, 15.9 mmol) and trichloroacetonitrile (155.5 mL, 1.55 mol). After stirring for 5.5 hours at ambient temperature, the reaction mixture is washed with water, washed with saturated NaCl solution, dried over MgSO₄, concentrated under reduced pressure, and azeotroped with toluene to give the product as a foam.

Preparation of (3β, 5β, 14β, 17β)-14-Amino-3-[(3', 6'-dideoxy-2', 4'-O-dibenzoyl-α-L-mannopyranosyl)-oxy]-androstane-17-carboxylic acid methyl ester

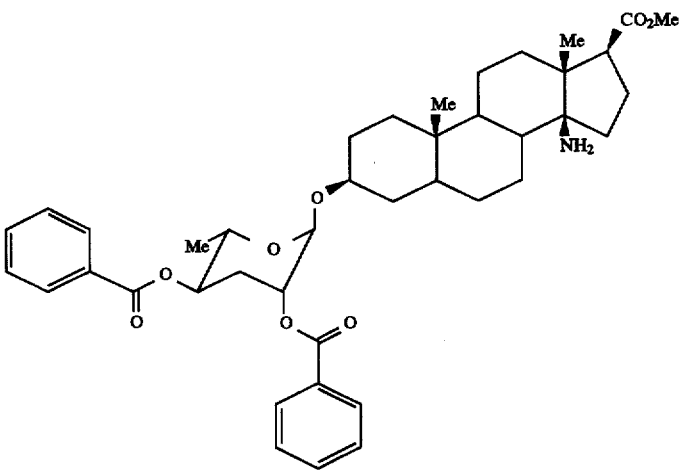

Molecular sieves (4 Å, 5 g) are added to a solution of (3β, 5β, 14β, 17β)-14-amino-3-hydroxy-androstane-17-carboxylic acid methyl ester (5.0 g, 14.3 mmol) [prepared as described U.S. Pat. No. 4,885,280, hereby incorporated by reference herein] and trimethylsilyltriflate (3.87 mL, 20.0 mmol) in CH₂Cl₂ (200 mL) and stirred for 2 hours at −25° C. to −15° C. A solution of 3,6-dideoxy-α-L-arabino-hexopyranose, 2,4-di-O-benzoate-1-(2,2,2-trichloroethanimidate) (8.17 g, 16.4 mmol) in CH₂Cl₂ (60 mL) is then added slowly over 5 hours while maintaining the temperature at −25° C. to −15° C. The reaction mixture is stirred for 16 hours. (If Thin-Layer Chromatography indicates the reaction is incomplete, more trimethylsilyl triflate and 3,6-dideoxy-α-L-arabino-hexopyranose, 2,4-di-O-benzoate-1-(2,2,2-trichloroethanimidate) may be added.) The reaction mixture is washed with saturated NaHCO₃ solution (250 mL). The aqueous layer is re-extracted with CH₂Cl₂ (2×100 mL) and the combined CH₂Cl₂ layers are washed with water (300 mL), and then with saturated NaCl solution (300 mL). The CH₂Cl₂ layer is dried over MgSO₄, and concentrated under reduced pressure to give the crude product.

Example 25

Synthesis of 3,6-Dideoxy-L-erythro-hex-2-enonic acid, δ-lactone, 2,4-O-dibenzoate

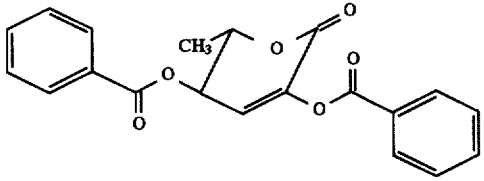

3,6-Dideoxy-L-erythro-hex-2-enonic acid, δ-lactone, 2,4-O-dibenzoate [prepared as described in Example 24 herein] can also be synthesized according to the procedures described below:

α-L-6-Deoxy-mannopyranose, monohydrate (10 g, 54.9 mmol) is added to DMF or acetonitrile (100–200 mL), followed by the addition of benzoyl peroxide (1.0 to 1.5 equivalents) and a suitable metal chloride or bromide (0.5 to 1.5 equivalents), such as, lithiium bromide, lithium chloride, nickel bromide, nickel chloride, etc. This reaction mixture is stirred for at 20° C. to 100° C. until complete, as indicated using Thin-Layer Chromatography.

A suitable base, such as, triethylamine (6.0 to 10.0 equivalents) is then added, followed by the addition of benzoyl chloride (3.0 to 5.0 equivalents). This is allowed to stir at 20° C. to 60° C. until complete, as indicated using Thin-Layer Chromatography. Water is then added to the reaction mixture and the product is extrated with a suitable solvent, such as, EtOAc. The combined organic extracts are washed with water, dried over NaSO4 and concentrated to give the crude product. This is then crystallized from EtOH to give the pure product as a white solid.

Example 26

Synthesis of (3β, 5β, 14β, 17β)-14-Amino-3-[(3', 6'-dideoxy-2', 4'-O-dibenzoyl-α-L-mannopyranosyl)-oxy]-androstane-17-carboxylic acid methyl ester (3β, 5β, 14β, 17β)-14-Amino-3-[(3', 6'-dideoxy-2', 4'-O-dibenzoyl-α-L-mannopyranosyl)-oxy]-androstane-17-carboxylic acid methyl ester [prepared as described in Example 9 and Example 24 herein] can also be synthesized according to the procedures described below:

Molecular sieves (4 Å, 0.5 g) are added to a solution of methanesulfonic anhydride (0.328 g, 1.88 mmol) in $CH_2Cl_2$ (10 mL) and stirred for 0.5 hour at 0° C. Triethylamine (0.4 mL, 2.7 mmol) and 3,6-dideoxy-a,b-L-arabino-hexopyranose 2,4-di-O-benzoate (0.611 g, 1.72 mmol [prepared according to the synthesis described in Example 24] are then added and stirring is continued for 30 minutes. (See the procedure as generally described in Leroux, J.; Perlin, A. S., *Carbohydrate Research* (1978) 67, 163, except triethylamine is used instead of s-collidine).

Methanesulfonic acid (0.1 mL, 1.54 mol) is then added, followed by the addition of (3β, 5β, 14β, 17β)-14-amino-3-hydroxy-androstane-17-carboxylic acid methyl ester (0.5 g, 1.43 mmol) [prepared as described in U.S. Pat. No. 4,885,280, hereby incorporated herein by reference]. The reaction mixture is allowed to warm to ambient temperature and is then stirred for 72 hours. The reaction mixture is filtered over Celite, washed with water (10 mL) and with saturated NaCl solution (10 mL). The $CH_2Cl_2$ layer is dried over $MgSO_4$, filtered, and evaporated to give the crude product, (3β, 5β, 14β, 17β)-14-amino-3-[(3', 6'-dideoxy-α-L-mannopyranosyl)-oxy]-androstane-17-carboxylic acid methyl ester, maleate.

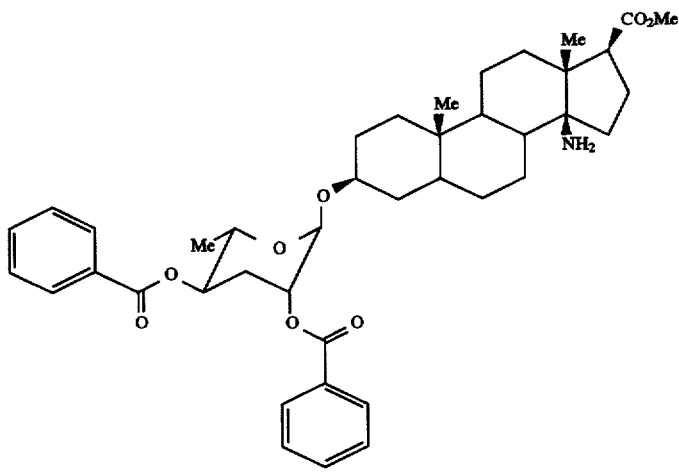

Example 27

Synthesis of (3β, 5β, 14β, 17β)-14-Amino-3-[(3', 6'-dideoxy-α-L-mannopyranosyl)-oxy]-androstane-17-carboxylic acid methyl ester

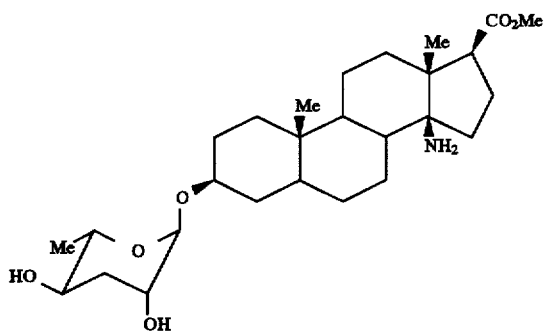

(3β, 5β, 14β, 17β)-14-Amino-3-[(3', 6'-dideoxy-α-L-mannopyranosyl)-oxy]-androstane-17-carboxylic acid methyl ester [prepared as described in Example 10 herein] can also be synthesized according to the procedure described below:

To a solution of (3β, 5β, 14β, 17β)-14-amino-3-[(3', 6'-dideoxy-2', 4'-O-dibenzoyl-α-L-mannopyranosyl)-oxy]-androstane-17-carboxylic acid methyl ester (200 g, 0.29 mol) [prepared as described in Example 26 herein] in a mixture of MeOH (2 L) and $CH_2Cl_2$ (1 L) is added NaOMe (16 g, 0.30 mol) with stirring at ambient temperature. The reaction mixture is allowed to stir for 24 hours and is then quenched by adding $NaHCO_3$ (54 g, 0.65 mol). This is stirred for 2 hours, filtered, and concentrated under reduced pressure to give an oily residue. The residue is then slurried in 10% heptane/methyl t-butyl ether (2.25 L) for 2 hours, filtered, and reslurried in water (1 L) for 2 hours. The product is obtained as a white solid upon filtration and drying.

Example 28

Synthesis of (3β, 5β, 14β, 17β)-14-Amino-3-[(3', 6'-dideoxy-α-L-mannopyranosyl)-oxy]-androstane-17-carboxylic acid methyl ester, maleate

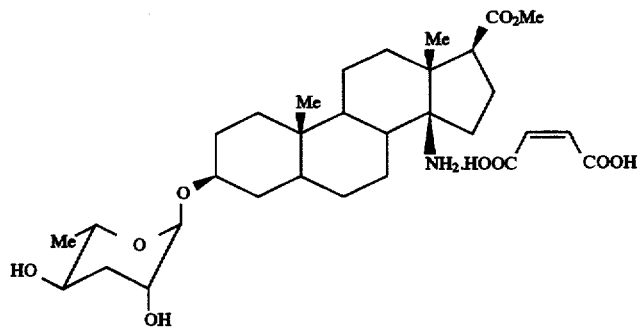

To the solution of crude (3β, 5β, 14β, 17β)-14-amino-3-[(3', 6'-dideoxy-2', 4'-O-dibenzoyl-α-L-mannopyranosyl)-oxy]-androstane-17-carboxylic acid methyl ester (15.0 g., 31.3 mmol) [prepared as described in Example 27 herein] in MeOH (50 mL) is added dropwise a solution of maleic acid (4.0 g, 34.5 mmol) in methanol. Acetone (200 mL) is then added and the mixture is cooled to 0° C. for 24 hours. The white crystalline product is then filtered and dried.

ASSESSMENT OF PHARMACOLOGICAL ACTIVITY

It is postulated that the positive inotropic effect of a cardiotonic steroid compound is due to its effect on the Na+, K+ pump in the sarcolemma of the cardiac muscle cells. Specifically, the cardiotonic steroids inhibit the Na+, K+-activated adenosine triphosphatase which in turn leads to an increase in intracellular calcium. Thus, more calcium is available to activate the contractile mechanism. See generally, Goodman and Gilman, *The Pharmacological Basis of Therapeutics*, Chapter 34 (8th Ed., 1990).

The positive inotropic activity of a new chemical entity is assessed both in isolated cardiac tissues and in whole animal models. The isolated tissue provides a direct measurement of the inotropic potential of a compound as the system is virtually free from metabolic, neurohormonal and absorption interferences which may influence the tissue response. The in vivo assays provide an assessment which takes into account those physiological parameters lacking in the isolated tissue assay.

In the assay for inotropic activity, papillary muscle strips from guinea pig hearts are utilized. Although the papillary muscle is involved more with valve function, the basic contractile response exhibited by this muscle is similar to that of ventricular muscle. For the assay, a segment of papillary muscle dissected from a guinea pig heart is suspended in an organ bath which provides the tissue with a temperature controlled, aqueous environment containing the substrates necessary for cellular function. By attaching a force transducer to the free end of the muscle strip such that the muscle is suspended between a fixed base and the transducer and applying an electrical stimulus, it is possible to measure shortening or contraction in response to various concentrations of test compounds. Under typical conditions, positive inotropy is defined as the increase in contractile force elicited by an unknown agent and the data is usually reported as the concentration of drug necessary to elicit a 50% increase in contractile force from baseline ($EC_{50}$).

The assessment of positive inotropy in vivo is made in two ways. The first is very similar to the measurement described for the in vivo method in that a strain gauge is sutured to the exterior of the heart to determine contractile force. In the second protocol, a force transducer is inserted into the left ventricle to detect pressure changes. The myocardial contractile force is correlated to the rate of pressure development within the left ventricle and is expressed as +dP/dt. In either case, the data is reported as the amount of drug necessary to achieve a level of activity such as 30% increase in contractility or +dP/dt (i.e., $ED_{30}$) and is expressed as mg drug/kg weight of the animal.

PHARMACEUTICAL COMPOSITIONS

The novel deoxy and oxygen-substituted sugar-containing 14-aminosteroid compounds of the present invention may be administered to humans or other mammals by a variety of routes, including, but not limited to, oral dosage forms and injections (intravenous, intramuscular, intraperitoneal and subcutaneous). Numerous other dosage forms containing the novel deoxy and oxygen-substituted sugar-containing 14-aminosteroid compounds of the present invention can be readily formulated by one skilled in the art, utilizing the suitable pharmaceutical excipients as defined below. For considerations of patient compliance, oral dosage forms are generally most preferred.

The term "pharmaceutical composition" as used herein means a combination comprised of a safe and effective amount of the novel deoxy and oxygen-substituted sugar-containing 14-aminosteroid compound active ingredient, or mixtures thereof, and pharmaceutically-acceptable excipients.

The phrase "safe and effective amount", as used herein, means an amount of a compound or composition large enough to significantly positively modify the symptoms and/or condition to be treated, but small enough to avoid serious side effects (at a reasonable benefit/risk ratio), within the scope of sound medical judgment. The safe and effective amount of active ingredient for use in the pharmaceutical compositions to be used in the method of the invention herein will vary with the particular condition being treated, the age and physical condition of the patient being treated, the severity of the condition, the duration of the treatment, the nature of concurrent therapy, the particular active ingredient being employed, the particular pharmaceutically-acceptable excipients utilized, and like factors within the knowledge and expertise of the attending physician.

The term "pharmaceutically-acceptable excipients" as used herein includes any physiologically inert, pharmacologically inactive material known to one skilled in the art, which is compatible with the physical and chemical characteristics of the particular deoxy or oxygen-substituted sugar containing 14-aminosteroid compound active ingredient selected for use. Pharmaceutically-acceptable excipients include, but are not limited to, polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

The term "oral dosage form" as used herein means any pharmaceutical composition intended to be systemically administered to an individual by delivering said composition to the gastrointestinal tract of an individual, via the mouth of said individual. For purposes of the present invention, the delivered form can be in the form of a tablet, coated or non-coated; solution; suspension; or a capsule, coated or non-coated.

The term "injection" as used herein means any pharmaceutical composition intended to be systemically administered to a human or other mammal, via delivery of a solution or emulsion containing the active ingredient, by puncturing the skin of said individual, in order to deliver said solution or emulsion to the circulatory system of the individual either by intravenous, intramuscular, intraperitoneal or subcutaneous injection.

The rate of systemic delivery can be satisfactorily controlled by one skilled in the art, by manipulating any one or more of the following:

(a) the active ingredient proper;

(b) the pharmaceutically-acceptable excipients; so long as the variants do not interfere in the activity of the particular active ingredient selected;

(c) the type of the excipient, and the concomitant desirable thickness and permeability (swelling properties) of said excipients;

(d) the time-dependent conditions of the excipient itself and/or within the excipients;

(e) the particle size of the granulated active ingredient; and (f) the pH-dependent conditions of the excipients.

As stated hereinabove, pharmaceutically-acceptable excipients include, but are not limited to, resins, fillers, binders, lubricants, solvents, glidants, disintegrants co-solvents, surfactants, preservatives, sweetener agents, flavoring agents, buffer systems, pharmaceutical-grade dyes or pigments, and viscosity agents.

The preferred solvent is water.

Flavoring agents among those useful herein include those described in *Remington's Pharmaceutical Sciences*, 18th Edition, Mack Publishing Company, 1990, pp. 1288–1300, incorporated by reference herein. The pharmaceutical compositions suitable for use herein generally contain from 0–2% flavoring agents.

Dyes or pigments among those useful herein include those described in *Handbook of Pharmaceutical Excipients*, pp. 81–90, 1986 by the American Pharmaceutical Association & the Pharmaceutical Society of Great Britain, incorporated by reference herein. The pharmaceutical compositions herein generally contain from 0–2% dyes or pigments.

Preferred co-solvents include, but are not limited to, ethanol, glycerin, propylene glycol, polyethylene glycols. The pharmaceutical compositions of the present invention include from 0–50% co-solvents.

Preferred buffer systems include, but are not limited to, acetic, boric, carbonic, phosphoric, succinic, malaic, tartaric, citric, acetic, benzoic, lactic, glyceric, gluconic, glutaric and glutamic acids and their sodium, potassium and ammonium salts. Particularly preferred are phosphoric, tartaric, citric, and acetic acids and salts. The pharmaceutical composition of the present invention generally contain from 0–5% buffer systems.

Preferred surfactants include, but are not limited to, polyoxyethylene sorbitan fatty acid esters, polyoxyethylene monoalkyl ethers, sucrose monoesters and lanolin esters and ethers, alkyl sulfate salts, sodium, potassium, and ammonium salts of fatty acids. The pharmaceutical compositions of the present invention include 0–2% surfactants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0–2% preservatives.

Preferred sweeteners include, but are not limited to, sucrose, glucose, saccharin, sorbitol, mannitol, and aspartame. Particularly preferred are sucrose and saccharin. Pharmaceutical compositions of the present invention include 0–5% sweeteners.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0–5% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0–75% fillers.

Preferred lubricants include, but are not limited to, magnesium stearate, stearic acid, and talc. The pharmaceutical compositions of the present invention include 0.5–2% lubricants.

Preferred glidants include, but are not limited to, talc and colloidal silicon dioxide. The compositions of the present invention include from 1–5% glidants.

Preferred disintegrants include, but are not limited to, starch, sodium starch glycolate, crospovidone, croscarmelose sodium, and microcrystalline cellulose. The pharmaceutical compositions of the present invention include from 4–15% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 1–10% binders.

Compounds of the present invention may comprise from 0.1% to 99.9% by weight of the pharmaceutical compositions of the present invention. Preferably the compounds of the present invention comprise from about 20% to about 80% by weight of the pharmaceutical compositions of the present invention.

Accordingly, the pharmaceutical compositions of the present invention include from 15–95% of a deoxy and oxygen-substituted sugar-containing 14-aminosteroid compound active ingredient, or mixture, thereof; 0–2% flavoring agents; 0–50% co-solvents; 0–5% buffer system; 0–2% surfactants; 0–2% preservatives; 0–5% sweeteners; 0–5% viscosity agents; 0–75% fillers; 0.5–2% lubricants; 1–5% glidants; 4–15% disintegrants; and 1–10% binders.

Suitable pharmaceutical compositions are described herein. It is well within the capabilities of one skilled in the art to vary the non-limiting examples described herein to achieve a broad range of pharmaceutical compositions.

The choice of a pharmaceutically-acceptable excipient to be used in conjunction with the deoxy or oxygen-substituted sugar-containing 14-aminosteroid compounds of the present invention is basically determined by the way the compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The preferred mode of administering the deoxy and oxygen-substituted sugar-containing 14-aminosteroid compounds of the present invention is orally. The preferred unit dosage form is therefore tablets, capsules and the like, comprising a safe and effective amount of the deoxy or oxygen-substituted sugar-containing 14-aminosteroid compounds of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

Various oral dosage forms can be used, including such solid forms as tablets, capsules, granules and bulk powders. These oral dosage forms comprise a safe and effective amount, preferably from 0.1 mg to 5.0 mg of the deoxy and oxygen-substituted sugar-containing 14-aminosteroid. More preferably these oral dosage forms comprise 0.25–1.0 mg of the deoxy and oxygen-substituted sugar-containing 14-aminosteroid. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents. Preferred carriers for oral administration include gelatin, propylene glycol, cottonseed oil and sesame oil.

The compositions of this invention can also be administered topically to a subject, i.e., by the direct laying on or spreading of the composition on the epidermal or epithelial tissue of the subject. Such compositions include, for example, lotions, creams, solutions, gels and solids. These topical compositions comprise a safe and effective amount, preferably from 0.5 mg to 2.0 mg, of the deoxy and oxygen-substituted sugar-containing 14-aminosteroid. More preferably these topical compositions comprise 1.0 mg of the deoxy and oxygen-substituted sugars-containing 14-aminosteroid. Suitable carriers for topical administration preferably remain in place on the skin as a continuous film, and resist being removed by perspiration or immersion in water. Generally, the carrier is organic in nature and capable of having dispersed or dissolved therein the deoxy and oxygen-substituted sugar-containing 14-aminosteroid. The carrier may include pharmaceutically-acceptable emollients, emulsifiers, thickening agents, and solvents.

The compositions of this invention can also be administered via the inhalation route. Such compositions are prepared in a matrix comprising a solvent such as water or a glycol, preservatives such as methyl or propyl paraben and propellants such as nitrogen or carbon dioxide.

Additionally, the compositions of this invention can be administered via a subcutaneous implant formed from silicone elastomers, ethylene vinyl acetate co-polymers or lactic-glycolic co-polymers.

In order to illustrate how to prepare pharmaceutical compositions containing the novel compounds of the present invention, the following non-limiting pharmaceutical composition examples are presented.

PHARMACEUTICAL COMPOSITION
EXAMPLES

Example 1

An immediate release oral dosage form (tablet) containing the (3$\beta$,5$\beta$,14$\beta$,17$\beta$)-14-Amino-3-[(2,4-di-O-acetyl-3,6- dideoxy-α-L-mannopyranosyl)oxy]androstane-17-carboxylic acid, methyl ester hydrochloride has the following composition:

| Active Ingredient | Amount |
|---|---|
| (3β,5β,14β,17β)-14-Amino-3-[(2,4-di-O-acetyl-3,6-dideoxy-α-L-mannopyranosyl)oxy]androstane-17-carboxylic acid, methyl ester hydrochloride | 1.0 mg |
| Excipients | |
| Microcrystalline cellulose | 28.5 mg |
| Lactose, hydrous | 67.2 mg |
| Crospovidone | 3.0 mg |
| Magnesium stearate | 0.3 mg |

Manufacturing Directions: (for 10,000 tablets)
1) 10.0 g of the drug, 285.0 g of microcrystalline cellulose, 672.0 g of lactose and 30.0 g of crospovidone are mixed in a Patterson-Kelley (PK) or other suitable blender,
2) the above mixture is blended with 3.0 g of magnesium stearate in a PK or suitable blender,
3) the above final blend is compacted into 100.0 mg tablets on a suitable tableting machine.

Example 2

A parenteral dosage form containing the (3β,5β,14β,17β)-14-Amino-3-[(6-deoxy-2,3,4-tri-O-acetyl-α-L-mannopyranosyl)oxy]-N-methylandrostane-17-carboxamide hydrochloride and suitable for use as an intravenous (I.V.) injection has the following composition:

| Active Ingredient | Amount |
|---|---|
| (3β,5β,14β,17β)-14-Amino-3-[(6-deoxy-2,3,4-tri-O-acetyl-α-L-mannopyranosyl)oxy]-N-methylandrostane-17-carboxamide hydrochloride | 1.0 mg |
| Excipients | |
| Mannitol | 200.0 mg |
| Citric acid/sodium citrate | quantity sufficient to adjust the pH between 5.5–6.5 |

Manufacturing Directions: (for 1000 vials)
1) 1.0 g of the drug, 200.0 g of mannitol and sufficient sodium citrate and citric acid are dissolved in 2200.0 ml of sterile, deionized water for injection,
2) the above solution is filtered through a 0.22 micron sterile membrane filter,
3) 2.2 ml of the above sterile solution is filled into Type I glass vials and then lyophilized in a suitable lyophilizer,
4) the vials, after lyophilization, are stoppered with bromobutyl or other suitable stoppers and sealed. The lyophilized product is reconstituted with 2.0 ml of sterile water for injection immediately prior to use.

Example 3

A sustained release oral dosage form (tablet) containing the (3β,5β,14β,17β)-14-Amino-3-[(3,6-dideoxy-α-L-mannopyranosyl)oxy]androstane-17-carboxylic acid, methyl ester has the following composition:

| Active Ingredient | Amount |
|---|---|
| (3β,5β,14β,17β)-14-Amino-3-[(3,6-dideoxy-α-L-mannopyranosyl)oxy]androstane-17-carboxylic acid, methyl ester | 5.0 mg |
| Excipients | |
| Hydroxypropylmethylcellulose | 120.0 mg |
| Lactose, hydrous | 120.0 mg |
| Magnesium stearate | 12.0 mg |
| Colloidal silicon dioxide | 4.0 mg |

Manufacturing Directions: (for 10,000 tablets)
1) 50.0 gm of the drug, 1.2 kg of hydroxypropylmethylcellulose and 1.2 kg of lactose are mixed intimately in a twin shell Patterson-Kelley or suitable mixer,
2) to the above mix are added 120 gm of magnesium stearate and 40 gm of colloidal silicon dioxide and this is lightly blended in a suitable mixer,
3) the above blend is compacted into tablets weighing 261.0 mg on a suitable tablet press.

MISCELLANEOUS EXAMPLES

In addition to the above three examples, the drug active ingredient is formulated into a number of different dosage forms:
1) a pharmaceutical aerosol containing solvent (e.g. water, glycols), preservatives (methyl or propyl parabens) and propellants (nitrogen, carbon dioxide) or other suitable excipients,
2) a rectal suppository containing theobroma oil or polyethylene glycols,
3) a subcutaneous implant containing silicone elastomers, ethylene-vinyl acetate copolymers, lactic-glycolic copolymers and hydrogels or other suitable polymers,
4) commercially available implantable devices,
5) a transdermal system containing silicone fluid in an ethylene-vinyl acetate copolymer membrane or other suitable ingredients for delivery with or without the aid of iontophoresis,
6) a buccal mucoadhesive patch containing hydrocolloid polymers (hydroxyethyl cellulose, hydroxy-propyl cellulose, povidone) and other suitable polymers.

METHODS OF TREATMENT

The term, Congestive Heart Failure "CHF" as used herein, denotes a progressive disease wherein the hemodynamic capacity as well as the structure of the heart itself is increasingly and irreversibly compromised. The progression of CHF according to the patient's symptoms has been classified into four functional classifications by the New York Heart Association (NYHA).

New York Heart Association

Functional Classification

Class

I. Patients with cardiac disease but without resulting limitations of physical activity. Ordinary physical activity does not cause undue fatigue, palpitation, dyspnea, or anginal pain.

II. Patients with cardiac disease resulting in slight limitation of physical activity. They are comfortable at rest. Ordinary physical activity results in fatigue, palpitation, dyspnea, or anginal pain.

III. Patients with cardiac disease resulting in marked limitation of physical activity. They are comfortable at rest. Less than ordinary physical activity causes fatigue, palpitation, dyspnea, or anginal pain.

IV. Patient with cardiac disease resulting in inability to carry on any physical activity without discomfort. Symptoms of cardiac insufficiency or of the anginal syndrome may be present even at rest. If any physical activity is undertaken, discomfort is increased.

NYHA Classes III and IV, also referred to as overt congestive heart failure, are often treated by administering compounds that increase cardiac contractility by exerting a positive inotropic effect. The reference compound for increasing cardiac contractility is oral digoxin. Treating the symptoms of the overt CHF by administering inotropes to increase CO to meet the metabolic needs of the body can improve the quality of life for a CHF patient because the heart can better supply the metabolic need of the body. Conventional wisdom, however, indicates that an inotrope, such as digitalis, might increase mortality rates because the inotropic action creates an extra work load for the heart. Furthermore, digitalis has a narrow therapeutic:toxic dose ratio and administration of digitalis at an earlier than Class III NYHA functional classification may not be prudent.

Additionally, the bipyridine inotrope, Milrinone, has been shown to aggravate ventricular arrhythmias and possibly increase mortality. See DiBianco, R., et al. "A Comparison of Oral Milrinone, Digoxin, and Their Combination in the Treatment of Patients with Chronic Heart Failure", *N. Engl. J. Med.* 320:677 (1989).

The term "hemodynamic" as used herein, refers to the mechanical capability of the heart. The initial hemodynamic consequence of heart failure is a decrease in stroke volume which is a measurement of the amount of blood ejected with each heart beat. The heart then compensates to increase the CO to maintain flow to the vital organs. As the heart failure worsens, intracardiac filling pressures are elevated as well as pulmonary and venous pressures. The heart is increasingly unable to supply the required CO.

The term "structural damage" as used herein, refers to the microscopic and macroscopic changes in the heart of a person suffering from CHF. Structurally, on a microscopic level the following changes occur: The early stage of cardiac hypertrophy is characterized morphologically by increases in the size of myofibrils and mitochondria as well as enlargement of mitochondria and nuclei. Muscle cells are larger than normal, but cellular organization is largely preserved. At a more advanced stage of hypertrophy, preferential increases in the size or number of specific organelles, such as mitochondria, as well as irregular addition of new contractile elements in localized areas of the cell, result in subtle abnormalities of cellular organization and contour. Adjacent cells may vary in their degree of enlargement.

Cells subjected to long-standing hypertrophy show more obvious disruptions in cellular organization, such as markedly enlarged nuclei with highly lobulated membranes, which displace adjacent myofibrils and cause breakdown of normal Z-band registration. The early preferential increase in mitochondria is supplanted by a predominance by volume of myofibrils. The late stage of hypertrophy is characterized by cell death and a loss of contractile elements with marked disruption of Z bands, severe disruption of the normal parallel arrangement of the sarcomeres, dilation and increased tortuosity of T tubules, and replacement of the contractile elements with fibrosis tissue. See Braunwald, *Heart Disease: A Textbook of Cardiovascular Medicine*, Vol. 1 (3rd ed. 1988). These microscopic changes are revealed on a macroscopic level by cardiac hypertrophy or enlargement of the heart. The hypertrophying heart becomes less efficient due to microscopic changes causing loss of contractile elements and fibrotic deposition and the patient's clinical symptoms worsen as he progresses through each NYHA functional classification.

The compounds of the present invention increase cardiac contractility. The dosage range can be between 0.1 mg and 5 mg per day as determined by the attending physician according to the mode of administration, the severity of the CHF and the duration of treatment.

In order to illustrate the particular utility of these unique deoxy and oxygen-substituted sugar-containing 14-aminosteroid compounds, for the treatment of CHF, the following non-limiting clinical examples are presented.

CLINICAL EXAMPLES

Example 1

An obese 65 year old white female with a 20 year history of non-insulin dependent diabetes mellitus and hypertension, and a myocardial infarction 2 years prior, is admitted to the coronary care unit after 12 hours of symptoms with an acute inferior myocardial infarction. Her hospital course is complicated by acute pulmonary edema which manifests itself by severe dyspnea at rest, orthopnea, jugular venous distention, bilateral rales to mid-scapula; a dilated heart and bilateral infiltrates on CXR. Her pulmonary capillary wedge pressure is 35 mmHg. She is treated with morphine, oxygen, intravenous nitroglycerin, a loop diuretic and 0.25 mg of (3β,5β,14β,17β)-14-Amino-3-[(2,4-di-O-acetyl-3,6-dideoxy-α-L-mannopyranosyl)oxy]androstane-17-carboxylic acid, methyl ester hydrochloride intravenously every 4 hours for three days, followed by 0.25 mg of (3β,5β,14β,17β)-14-Amino-3-[(2,4-di-O-acetyl-3,6-dideoxy-α-L-mannopyranosyl)oxy]androstane-17-carboxylic acid, methyl ester hydrochloride orally once a day. She improves on this regimen and is discharged in 10 days with dyspnea on mild exertion (mild congestive heart failure, NYHA Class II) to be followed as an outpatient on a diuretic, ACE inhibitor, nitroglycerin and 0.25 mg orally of (3β,5β,14β,17β)-14-Amino-3-[(2,4-di-O-acetyl-3,6-dideoxy-α-L-mannopyranosyl)oxy]androstane-17-carboxylic Acid, methyl ester hydrochloride per day.

Example 2

A 44-year old black male with a history of long-standing uncontrolled hypertension and a one year history of moderate (NYHA Class III) congestive heart failure presents with several episodes of presyncope over the preceding 2 weeks. He also complains of fatigue and dyspnea when getting dressed. Medications include digoxin (0.25 mg/day), lasix and ACE inhibitor. He has an S3 gallop, pitting ankle edema, left ventricular hypertrophy and occasional PVCs on ECG. Additional evaluation discloses frequent multifocal ventricular ectopy and a run of non-sustained ventricular tachycardia on Holter monitoring, an ejection fraction of 30% by radionuclide ventriculography and a serum digoxin level of 2.2 ng/ml. The arrhythmias and pre-syncope are suspected to be a result of digitalis toxicity, and the drug is discontinued. (3β,5β,14β,17β)-14-Amino-3-[(6-deoxy-2,3,4-tri-O-acetyl-α-L-mannopyranosyl) oxy]-N-methylandrostane-17-carboxamide hydrochloride is instituted at an oral dose of 0.25 mg per day. Because of persistence of fatigue and dyspnea, the dose is increased over the next six weeks to 1 mg daily with no additional episodes of pre-syncope, a reduction of PVCs and absence of nonsustained ventricular tachycardia on repeat Holter and an increase in the ejection fraction to 38%. His dyspnea with self-care activities such as dressing is resolved and he is able to work in his garden with mild occasional dyspnea (NYHA Class II). At one year follow-up his condition is unchanged.

Example 3

A 24 year-old previously healthy Chinese female presents with a two month history of dyspnea with strenuous exertion. There is no family history of heart disease; she is a non-smoker, and does not drink alcohol. Physical exam is normal with the exception of tachycardia and a laterally displaced point of maximum impulse. A heart rate of 105 and non-specific T wave flattening are seen on ECG, and CXR reveals an enlarged heart. Echocardiogram shows biventricular enlargement with global hypokinesia, and an ejection fraction of 40%. The valves appear normal. A symptom limited treadmill exercise test shows no evidence of ischemia. A diagnosis of idiopathic dilated cardiomyopathy, NYHA Class I, is made. Initial treatment with an ACE inhibitor produces an intolerable cough, and is therefore discontinued. (3β,5β,14β,17β)-14-amino-3-[(3,6-dideoxy-α-L-mannopyranosyl)oxy]androstane-17-carboxylic acid, methyl ester is administered orally at a dosage of 1 mg twice a day, and over the next month her ability to exercise improves. There is also an increase in the ejection fraction (by echocardiogram) to 55%, and an increase in exercise time of 200 seconds on the treadmill exercise test.

Example 4

A 55 year old white male with a history of two previous myocardial infarctions and whose father died suddenly at age 50, is being maintained on isosorbide dinitrate and a beta blocker with stable effort angina for two years. Over the preceding month, however, he develops dyspnea on walking up one flight of stairs, swelling of the ankles at night and occasional paroxysmal nocturnal dyspnea.

He has a resting heart rate of 90, 1+ pitting edema of the ankles, an S3 gallop, an enlarged heart and Kerly B lines on CXR. A diagnosis of mild (NYHA Class II) congestive heart failure due to ischemic heart disease is made. His beta blocker is discontinued by gradual tapering, and an ACE inhibitor and diuretic added, but on this new regimen his congestive heart failure worsens. (3β,5β,14β,17β)-14-Amino-3-[(2,3,6-trideoxy-α-L-mannopyranosyl)oxy]androstane-17-carboxylic acid, methyl ester is orally administered at a dose of 4 mg once daily. His dyspnea and edema resolves (NYHA Class I), heart rate decreased to 75, S3 disappeared, heart size decreases and congestion on CXR resolves. There is an increase in exercise time of 170 seconds on his treadmill test performed 1 month later. No further worsening occurs over the next 2 years.

Example 5

A 60 year old black female who has a history of three myocardial infarctions and resultant severe (NYHA Class IV) congestive heart failure has been hospitalized with four times in the preceding six weeks for acute decompensation despite therapy with maximally tolerated doses of lasix, isosorbide dinitrate, digoxin, and an ACE inhibitor. Her symptoms include edema, dyspnea at rest, 3 pillow orthopnea, marked fatigue and mental confusion. A decision is made to discontinue the digoxin and institute treatment with (3β,5β,14β,17β)-14-Amino-3-[(2',6'-dideoxy-2',2'-difluoro-α-L-mannopyranosyl)-oxy]-androstane-17-carboxylic acid methyl ester. The initial dose of (3β, 5β, 14β, 17β)-14-Amino-3-[(2',6'-dideoxy-2',2'-difluoro-α-L-mannopyranosyl)-oxy]-androstane-17-carboxylic acid methyl ester is 0.5 mg orally administered once a day, but titration to 2 mg three times a day is required over a 2 month period to adequately control her symptoms. At the end of the two month period, her orthopnea, confusion and edema resolve; and she has an improved ability to perform activities of daily living such as dressing herself without dyspnea (NYHA Class III, moderate congestive heart failure). Her ejection fraction also improves from 20 to 35%. She remains stable over the following three months.

Example 6

A recently (2 months) sober 60 year old white male alcoholic, with a 30 year history of cigarette smoking is admitted to the hospital with a three month history of progressively worsening dyspnea on exertion, fatigue, orthopnea, edema and paroxysmal nocturnal dyspnea. He has dyspnea while brushing his teeth. Physical examination reveals a cachectic male in moderate distress with a respiratory rate of 30 per minute, a heart rate or 110 bpm, blood pressure 90/50, an S3 gallop, 2+ pitting edema to the knees, jugular venous distention, hepatomegaly, ascites, bibasilar rales and an enlarged heart. Extensive evaluation provides diagnoses of chronic alcoholic hepatitis, chronic obstructive pulmonary disease, and moderate (NYHA Class III) congestive heart failure due to toxic (alcoholic) cardiomyopathy. Treatment is begun with hydrochlorthiazide, an ACE inhibitor and (3β, 5β, 14β, 17β)-14-Amino-3-[(2',3',6'-trideoxy-2',2'-difluoro-α-L-mannopyranosyl)-oxy]-androstane-17-carboxylic acid methyl ester at a daily oral dose of 0.25 mg per day. He improves rapidly and is discharged in a week. After a 20 pound weight loss he is able to walk to the mailbox with mild dyspnea (NYHA Class II). His respiratory rate is 20, heart rate 90, the S3 is no longer audible, and the edema and rales resolve. The hepatomegaly persists unchanged, but the ascites is slightly diminished. The ejection fraction increases from 32 to 45% and the heart size decreases.

Example 7

A 70 year old sedentary white female is noted to have an enlarged heart on CXR done prior to elective surgery for a cataract. She denies any history of chest pain, dyspnea or any history of hypertension, diabetes or cardiac disease. Her ECG shows non-specific ST-T wave changes; and standard clinical laboratory evaluations are normal. A treadmill exercise test is terminated due to fatigue without evidence of coronary artery disease. An echocardiogram shows biventricular enlargement, normal valves and an ejection fraction of 30%. She is given a preventative course of (3β, 5β, 14β, 17β)-14-Amino-3-[(6'-deoxy-3'-3'-difluoro-α-L-mannopyranosyl)-oxy]-androstane-17-carboxylic acid methyl ester at 0.25 mg orally per day. Her ejection fraction increases to 40% and she is asymptomatic at the time of hospitalization for surgery for a second cataract 5 years later.

What is claimed is:

1. Deoxy and oxygen-substituted saccharide-containing 14-aminosteroid compounds and the pharmaceutically-acceptable acid salts or esters thereof of the general formula:

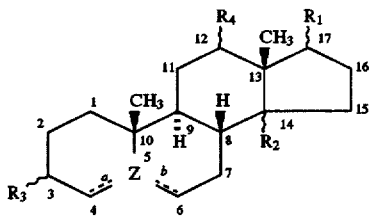

wherein a) $R_1$ is
  (i) $COOR_5$, where
    $R_5$ is a 1-6 carbon lower alkyl group; a 1-6 carbon lower alkyl group substituted by an amino group; an arylalkyl or heteroarylalkyl group or a carbocyclic ring, or
  (ii) $CHR_6OH$, where
    $R_6$ is a hydrogen atom or a 1-6 carbon lower alkyl group, or
  (iii) $COR'''$ where $R'''$ is hydrogen; 1-6 carbon lower alkyl; 1-6 carbon lower alkyl substituted amino; amino or dialkylamino, and b) $R_2$ is $-NR_7R_8$, where
    $R_7$ and $R_8$, which may be the same or different, are hydrogen atoms or a 1-6 carbon lower alkyl group; and c) $R_3$ is
  (i) a deoxy or oxygen-substituted monosaccharide residue,

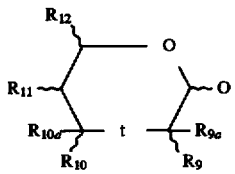

wherein $R_{9a}$, $R_9$, $R_{10}$, and $R_{10a}$, which may be the same or different, are 1-6 carbon lower alkyl; hydrogen; hydroxy; fluorine; alkoxy; acetoxy; arylalkyloxy; heteroarylalkyloxy or benzoxy; $R_{11}$ is 1-6 carbon lower alkyl; hydrogen; hydroxy; fluorine; benzoxy; arylalkyloxy; heteroarylalkyloxy; acetoxy or alkoxy; wherein further when $R_5$ is 1-6 carbon lower alkyl; either $R_9$, $R_{10}$ or $R_{11}$ cannot be hydroxy or acetoxy; further provided that when $R_{9a}$ is hydrogen and $R_{10a}$ is hydrogen and $R_9$ is hydrogen; hydroxy or acetoxy; and $R_{11}$ is hydroxy; acetoxy or alkoxy; $R_{10}$ cannot be hydroxy or acetoxy; and $R_{12}$ is methyl; acetoxymethyl or hydroxymethyl; t can be a single or double bond, or (ii) a deoxy or oxygen-substituted monosaccharide residue,

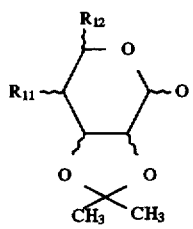

wherein $R_{11}$ is arylalkyloxy or heteroarylalkyloxy or 1-6 carbon lower alkyl substituted oxosilane and $R_{12}$ is methyl; and d) $R_4$ is
  (i) OH, or
  (ii) H, or
  (iii) $OR_{13}$, where $R_{13}$ is a monosaccharide residue; acetoxy; benzoxy, arylalkyl or heteroarylalkyl; and e) Z is
  (i) $-CH-$, where a and b are single bonds, or
  (ii) $=C$, where either a or b is a double bond.

2. A compound according to claim 1, wherein $R_1$ is $COOR_5$ and $R_5$ is a 1-6 carbon lower alkyl; $R_2$ is $NH_2$; $R_3$ is a deoxy and oxygen-substituted saccharide residue,

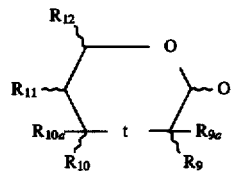

wherein $R_{9a}$, $R_9$, $R_{10}$, and $R_{10a}$, which may be the same or different, are 1-6 carbon lower alkyl; hydrogen; hydroxy; fluorine; alkoxy; acetoxy; arylalkyloxy; heteroarylalkyloxy; or benzoxy; $R_{11}$ is 1-6 carbon lower alkyl; hydrogen; hydroxy; fluorine; benzoxy; arylalkyloxy; heteroarylalkyloxy; acetoxy; or alkoxy; wherein further when $R_5$ is 1-6 carbon lower alkyl; either $R_9$, $R_{10}$, or $R_{11}$ cannot be hydroxy or acetoxy; further provided that when $R_{9a}$ is hydrogen and $R_{10a}$ is hydrogen and $R_9$ is hydrogen; hydroxy or acetoxy; and $R_{11}$ is hydroxy; acetoxy or alkoxy; $R_{10}$ cannot be hydroxy or acetoxy; and $R_{12}$ is methyl; acetoxymethyl or hydroxymethyl; t can be a single or double bond.

3. A compound according to claim 2, wherein $R_{9a}$ is hydrogen; $R_9$ is acetoxy; $R_{10}$ is hydrogen; $R_{10a}$ is hydrogen; $R_{11}$ is acetoxy.

4. A compound according to claim 2, wherein $R_{9a}$ is hydrogen; $R_9$ is arylalkyloxy; heteroarylalkyloxy; $R_{10}$ is hydrogen; $R_{10a}$ is hydrogen; $R_{11}$ is arylalkyloxy; heteroarylalkyloxy.

5. A compound according to claim 2, wherein $R_{9a}$ is hydrogen; $R_9$ is arylalkyloxy; heteroarylalkyloxy; $R_{10}$ is hydrogen; $R_{10a}$ is hydrogen; $R_{11}$ is hydroxy.

6. A compound according to claim 2, wherein $R_{9a}$ is hydrogen; $R_9$ is hydroxy; $R_{10}$ is hydrogen; $R_{11}$ is hydroxy.

7. A compound according to claim 2, wherein $R_{9a}$ is hydrogen; $R_9$ is hydroxy; $R_{10}$ is hydroxy; $R_{10a}$ is hydrogen; $R_{11}$ is arylalkyloxy; heteroarylalkyloxy.

8. A compound according to claim 2, wherein $R_{9a}$ is hydrogen; $R_9$ is hydrogen; $R_{10}$ is hydrogen; $R_{10a}$ is hydrogen; $R_{11}$ is arylalkyloxy; heteroarylalkyloxy.

9. A compound according to claim 2, wherein $R_{9a}$ is hydrogen; $R_9$ is hydrogen; $R_{10}$ is hydrogen; $R_{10a}$ is hydrogen; $R_{11}$ is hydroxy.

10. A compound according to claim 2, wherein $R_{9a}$ is hydrogen; $R_9$ is hydroxy; $R_{10}$ is hydrogen; $R_{10a}$ is hydrogen; $R_{11}$ is hydroxy.

11. A compound according to claim 2, wherein $R_{9a}$ is hydrogen; $R_9$ is hydrogen; $R_{10}$ is hydrogen; and $R_{11}$ is arylalkyloxy; heteroarylalkyloxy and benzoxy.

12. A compound according to claim 2, wherein $R_{9a}$ is hydrogen; $R_9$ is hydroxy; $R_{10}$ is hydrogen; $R_{10a}$ is hydrogen; $R_{11}$ is arylalkyloxy; heteroarylalkyloxy and benzoxy.

13. A compound according to claim 2, wherein $R_{9a}$ is hydrogen; $R_9$ is hydrogen; $R_{10}$ is hydrogen; $R_{10a}$ is hydrogen; $R_{11}$ is alkoxy.

14. A compound according to claim 2, wherein $R_{9a}$ is fluorine or methyl.

15. A compound according to claim 1, wherein $R_1$ is $COOR_5$ and $R_5$ is a 1-6 carbon lower alkyl; $R_2$ is $NH_2$; $R_3$ is a deoxy and oxygen-substituted saccharide residue,

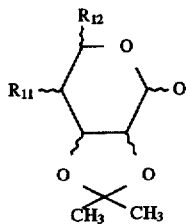

wherein $R_{11}$ is arylalkyloxy; heteroarylalkyloxy or 1-6 carbon lower alkyl substituted oxosilane and $R_{12}$ is methyl.

16. A compound according to claim 15 wherein $R_{11}$ is arylalkyloxy; heteroarylalkyloxy.

17. A compound according to claim 1, wherein $R_1$ is COR''' and R''' is methylamino; $R_2$ is $NH_2$; $R_3$ is a deoxy and oxygen-substituted saccharide residue,

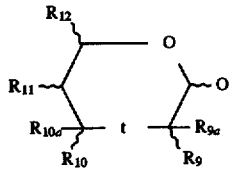

wherein $R_{9a}$, $R_9$, $R_{10}$, and $R_{10a}$, which may be the same or different, are 1-6 carbon lower alkyl; hydrogen; hydroxy; fluorine; alkoxy; acetoxyl; arylalkyloxy; heteroarylalkyloxy; or benzoxy; $R_{11}$ is 1-6 carbon lower alkyl; hydrogen; hydroxy; fluorine; benzoxy; arylalkyloxy; heteroarylalkyloxy; acetoxy; or alkoxy; $R_{12}$ is methyl; acetoxymethyl or hydroxymethyl; t can be a single or double bond.

18. A compound according to claim 17, wherein $R_{9a}$ is hydrogen, $R_9$ is acetoxy or hydroxy; $R_{10}$ is acetoxy or hydroxy; $R_{10a}$ is hydrogen; $R_{11}$ is acetoxy or hydroxy.

19. A compound according to claim 1, selected from the group consisting of (3β,5β,14β,17β)-14-Amino-3-[(2,4-di-O-acetyl-3,6-dideoxy-α-L-mannopyranosyl)oxy] androstane-17-carboxylic acid, methyl ester hydrochloride; (3β,5β,14β,17β)-14-Amino-3-[(6-deoxy-2,3,4-tri-O-acetyl-α-L-mannopyranosyl)oxy]-N-methylandrostane-17-carboxamide hydrochloride; (3β,5β,14β,17β)-14-Amino-3-[(3,6-dideoxy-α-L-mannopyranosyl)oxy]androstane-17-carboxylic acid, methyl ester; (3β,5β,14β,17β)-14-Amino-3-[(2,3,6-trideoxy-β-L-mannopyranosyl)oxy]androstane-17-carboxylic acid, methyl ester; (3β, 5β, 14β, 17β)-14-Amino-3-[(2',6'-dideoxy-2',2'-difluoro-α-L-mannopyranosyl)-oxy]-androstane-17-carboxylic acid methyl ester; (3β, 5β, 14β, 17β)-14-Amino-3-[(2',3',6'-trideoxy-2',2'-difluoro-α-L-mannopyranosyl)-oxy]-androstane-17-carboxylic acid methyl ester; (3β, 5β, 14β, 17β)-14-Amino-3-[(6'-deoxy-3'-3'-difluoro-α-L-mannopyranosyl)-oxy]-androstane-17-carboxylic acid methyl ester synthesis of (3β, 5β, 14β, 17β)-14-amino-3-[(3', 6'-dideoxy-α-L-mannopyranosyl)-oxy]-androstane-17-carboxylic acid methyl ester, maleate.

20. A pharmaceutical composition comprised, by weight, of a safe and effective amount for treating cardiac disease of from 15 to 95% of a compound of claim 1, or mixtures thereof, and from 5 to 85% pharmaceutically-acceptable excipients.

21. A pharmaceutical composition according to claim 20, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

22. A pharmaceutical composition according to claim 20 comprised, by weight, of from 15-95% of a compound of claim 1 (or mixtures thereof) 0-2% flavoring agents, 0-60% co-solvents; 0-5% buffer system; 0-2% surfactants; 0-2% preservatives; 0-5% sweeteners; 0-5% viscosity agents; 0-75% fillers; 0.5-2% lubricants; 1-5% glidants; 4-15% disintegrants; and 1-10% binders.

23. A pharmaceutical composition comprised, by weight, of a safe and effective amount for treating cardiac disease of from 15 to 95% of a compound of claim 2, or mixtures thereof, and from 5 to 85% pharmaceutically-acceptable ingredients.

24. A pharmaceutical composition according to claim 22, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

25. A pharmaceutical composition according to claim 23 comprised, by weight, of from 15-95% of a compound of claim 2 (or mixtures thereof); 0-2% flavoring agents; 0-50% co-solvents; 0-5% buffer system; 0-2% surfactants; 0-2% preservatives; 0-5% sweeteners; 0-5% viscosity agents; 0-75% fillers; 0.5-2% lubricants; 1-5% glidants; 4-15% disintegrants; and 1-10% binders.

26. A pharmaceutical composition comprised, by weight, of a safe and effective amount for treating cardiac disease of from 15-95% of a compound of claim 15, or mixtures thereof, and from 5-85% pharmaceutically-acceptable ingredients.

27. A pharmaceutical composition according to claim 25, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

28. A pharmaceutical composition according to claim 26 comprised, by weight, of from 15-95% of a compound of claim 15 (or mixtures thereof); 0-2% flavoring agents; 0-50% co-solvents; 0-5% buffer system; 0-2% surfactants; 0-2% preservatives; 0-5% sweeteners; 0-5% viscosity agents; 0-75% fillers; 0.5-2% lubricants; 1-5% glidants; 4-15% disintegrants; and 1-10% binders.

29. A pharmaceutical composition comprised, by weight, of a safe and effective amount for treating cardiac disease of from 15 to 95% of a compound of claim 17, or mixtures thereof, and from 5 to 85% pharmaceutically-acceptable excipients.

30. A pharmaceutical composition according to claim 28, wherein the pharmaceutically-acceptable excipients are selected from the group consisting of polymers, resins, plasticizers, fillers, binders, lubricants, glidants, disintegrants, solvents, co-solvents, buffer systems, surfactants, preservatives, sweetening agents, flavoring agents, pharmaceutical grade dyes or pigments, and viscosity agents.

31. A pharmaceutical composition according to claim 29 comprised, by weight, of from 15-95% of a compound of claim 17 (or mixtures thereof); 0-2% flavoring agents, 0-50% co-solvents, 0-5% buffer system; 0-2% surfactants;

0–2% preservatives; 0–5% sweeteners; 0–5% viscosity agents; 0–75% fillers; 0.5–2% lubricants; 1–5% glidants; 4–15% disintegrants; and 1–10% binders.

32. A method of treatment for humans or other mammals afflicted with congestive heart failure comprising administering to said human or other mammal a safe and effective amount for treating cardiac disease of the pharmaceutical composition of claim 20.

33. A method of treatment for humans or other mammals afflicted with congestive heart failure comprising administering to said human or other mammal a safe and effective amount for treating cardiac disease of the pharmaceutical composition of claim 22.

34. A method of treatment for humans or other mammals afflicted with congestive heart failure comprising administering to said human or other mammal a safe and effective amount for treating cardiac disease of the pharmaceutical composition of claim 25.

35. A method of treatment for humans or other mammals afflicted with congestive heart failure comprising administering to said human or other mammal a safe and effective amount for treating cardiac disease of the pharmaceutical composition of claim 28.

36. A method of making the compound of claim 1, wherein a compound having the structure:

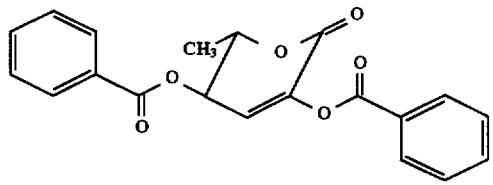

is used as a starting material or is formed as an intermediate in said method.

37. A method of making the compound having the structure:

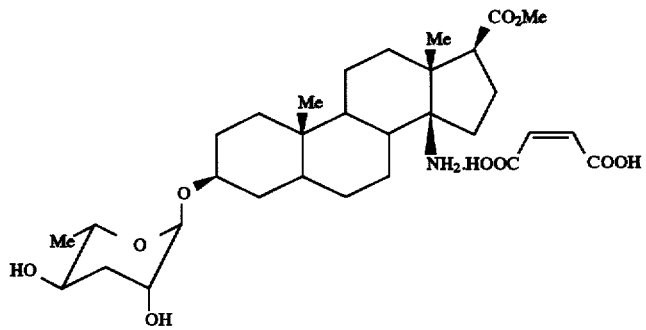

wherein the compound of claim 36 is used as a starting material in said method.

* * * * *